United States Patent

Fleck et al.

[11] Patent Number: 5,962,697
[45] Date of Patent: Oct. 5, 1999

[54] OPTICALLY ACTIVE 3-(1-(ALKYLAMINO)) ALKYL PYRROLIDINES

[75] Inventors: Thomas J. Fleck, Scotts; Bruce A. Pearlman, Kalamazoo; William W. McWhorter, Jr., Parchment, all of Mich.

[73] Assignee: Pharmacia & Upjohn Company, Kalamazoo, Mich.

[21] Appl. No.: 08/899,682

[22] Filed: Jul. 24, 1997

Related U.S. Application Data

[62] Division of application No. 08/549,793, May 3, 1994, Pat. No. 5,773,610, which is a continuation of application No. PCT/US94/04548, May 3, 1994, which is a continuation-in-part of application No. 08/058,611, May 6, 1993, abandoned.

[51] Int. Cl.[6] ........................ C07D 207/09; C07D 207/12
[52] U.S. Cl. ........................... 548/566; 548/579; 548/550
[58] Field of Search ..................................... 548/579, 566

[56] References Cited

PUBLICATIONS

Domagala, John M. et al., Quinolone Antibacterials Containing the New 7-[3-(1-Aminoethyl)-1-pyrrolidinyl] Side Chain, J. Med. Chem. (36) pp. 871–872, Apr. 1993.

Schroeder, Mel. C. et al., Synthesis of the Four Stereoisomers of Several 3-(1-Aminoethyl)pyrrolidines, Oct. 1992.

*Primary Examiner*—Johann Richter
*Assistant Examiner*—Dominic Keating
*Attorney, Agent, or Firm*—Thomas A. Wootton

[57] ABSTRACT

This invention relates to processes for the synthesis of various optically active amino pyrrolidinyl stereoisomers, or enantiomers, that may be attached to quinolonecarboxylic acids or naphthyridones. Processes and essential intermediates are disclosed and claimed for the synthesis of compounds represented by the structure shown in figure $BG_{4-1}$, below.

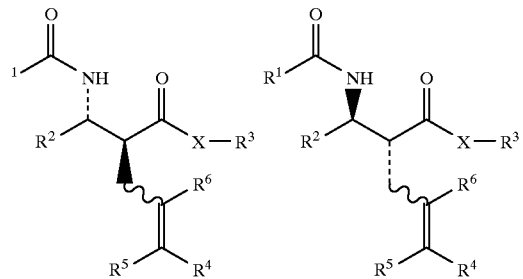

Figure $BG_{4-1}$ where $R^{50}$, $R^6$ and $R^9$ are defined independently and are H, —$(C_1-C_8)$alkyl, —$(C_3-C_8)$cycloalkyl, —$(C_1-C_8)$alkyl-$(C_3-C_8)$cycloalkyl, —$(C_6-C_{12}$ aryl), —$(C_1-C_8)$alkyl-$(C_6-C_{12}$ aryl), or the aryl or alkyl is substituted with one to three of the following groups, $(C_6-C_{12}$ aryl), $(C_1-C_3)$alkyl, $(C_1-C_3)$ alkoxy, halogen, trifluoromethyl;

where $R^2$ is —$(C_1-C_8)$alkyl, —$(C_3-C_8)$cycloalkyl, —$(C_1-C_8)$alkyl-$(C_3-C_8)$cycloalkyl, —$(C_6-C_{12}$ aryl), —$(C_1-C_8)$alkyl-$(C_6-C_{12}$ aryl), or the aryl or alkyl is substituted with one to three of the following groups, —$(C_6-C_{12}$ aryl), —$(C_1-C_3)$alkyl, —$(C_1-C_3)$ alkoxy, halogen, trifluoromethyl;

depending upon the starting materials used, compounds represented by the structure shown by figure $BG_{4-1}$ may have one of either of the two steriochemical arrangments shown, or, if the starting materials are a racemic mixture, the reaction may produce a 1:1 ratio of the combination of products shown in Figure $BG_{4-1}$, i.e. a racemic mixture.

6 Claims, No Drawings

OPTICALLY ACTIVE 3-(1-(ALKYLAMINO)) ALKYL PYRROLIDINES

CROSS-REFERENCE TO RELATED APPLICATIONS

The present patent application is a divisional U.S. patent application Ser. No. No. 08/549,793 with a filing date of May 3, 1994 of U.S. Pat. No. 5,773,610, that issued Jun. 30, 1998, which was a continuation (national phase) of PCT/US94/04548 filed May 3, 1994 which was a continuation-in-part of U.S. patent application Ser. No. 08/058,611 filed May 6, 1993, abandoned.

FIELD OF THE INVENTION

This method allows the convenient, large scale preparation for compounds, possibly used as intermediates of quinolones, in high optical purity and good yield. Previously published methods lack adequate stereoselectivity for large scale preparation or are impractical for large scale preparation.

BACKGROUND OF THE INVENTION

The quinolonecarboxylic acid based antibacterial agents such as norfloxacin and ciprofloxacin, now used clinically, exhibit potent antibacterial activity. Efforts to synthesize or discover a quinolone based antibacterial compound exhibiting maximum antibacterial properties and minimum toxic side effects continue. Many investigators have focused their efforts on developing quinolones with aminoalkyl pyrrolidinyl moieties attached to the 7 position of the quinolone.

Within the chiral environment of living organisms, individual stereoisomers of biologically active compounds are often known to have unique properties relative to their related stereoisomers. In vitro and in vivo studies of quinolone derivatives with various aminoalkyl pyrrolidinyl 7 position side chains have shown that the activity of these compounds can be strongly influenced by the stereochemical positions of the atoms in the side chain. European Patent Application—Publication 0,443,498 A1, published Aug. 28, 1991, discloses an aminoalkyl pyrrolidinyl 7 position side chain quinolones having 2 asymmetric carbon atoms on a 3-amino-4-methylpyrrolidine ring attached to the 7 position of a quinolone. Two of the four possible stereochemical isomers were two to six times more active than the other two stereoisomers. U.S. Pat. No. 5,157,128, issued Oct. 20, 1992, (Hagen) describes the effect of stereospecific alkylation at the 1'-aminoethyl position of a 3-pyrrolidine substituent also substituted at the 7 position of a quinolone. Hagen reported that the R-(1,1-dialkylated-1-aminomethyl) pyrrolidine, when coupled at the 7 position of a quinolone leads to antibacterial agents with improved activity and safety.

This invention relates to a process for the synthesis of various optically active amino pyrrolidinyl stereoisomers, or enantiomers, that may be attached to quinolonecarboxylic acids or naphthyridones. The process disclosed by the procedures and examples herein allow the synthesis of these side chains in a more efficient manner than any previously disclosed method of synthesis. Novel intermediates are also disclosed.

INFORMATION DISCLOSURE

Kokai Patent Application No. Hei 3 (1991)-72476, discloses the preparation of similar compounds using a less selective method of synthesis. Another less selective method of synthesis is provided in the Journal of Heterocyclic Chemistry, Vol. 29, No. 6, pp. 1481–98 (1992), also mentioned below. U.S. Pat. No. 5,157,128 issued Oct. 20, 1992, (Hagen), discloses optically pure isomers of 7-(3-(1,1-dialkylmethyl-1-amino)-1-pyrrolidinyl quinolones and naphthyridones and their method of manufacture. Guanti, Giuseppe, et al. in Tetrahedron Letter, Vol. 28, No. 37, pp 4335–4338 (1987) discuss a stereocontrolled synthesis of 3-(1'-hydroxyethyl)-2-azetidinones through trimethylsilyl trifluoromethanesulphonate catalyzed condensation of silyl ketene acetal. Estermann and Seebach, Helvetica Chimica Acta, Vol. 71 pp. 1824–39 (1988) discloses diastereoselective alkylation of N-protected 3-aminobutanoic acid esters at the 2 position. Seebach and Esterman, Tetrahedron Letters, Vol.28, No. 27 pp. 3310–3106 (1987) add additional discussion concerning alkylation of benzaldehyde to give enantiomerically pure 3-aminobutanoic acid derivatives. Furukawa et. al., Chemical Pharmaceutical Bulletin, Vol. 27. pp. 2223–6 at 6 (1979) discloses the use of Pearlman's reagent, 10% palladium hydroxide on charcoal, to hydrogenolytically remove benzyl groups from amines. The protection of the amino group with protecting groups such as carboxy benzyl are disclosed in Helvetica Chimica Acta, Vol. 66, Fasc. 2, Nr. 38, p. 461 (1983). Davies, in both Tetrahedron:Asymmetry, Vol. 2, No. 3, pp. 183–186 (1991) and in commercial literature, see, "Chiral Lithium Organoamide Technology Available," from Oxford Asymmetry Limited, Oxfordshire, UK. (Lithium Link), discloses the use of lithium organoamides in stereoselective Michael additions to crotonate esters. Orsini et. al., Synthetic Communications, Vol. 12, No. 14, pp. 1147–54 (1982) and Davis et. al., Journal of the American Chemical Society, Vol. 109, No. 11, pp. 3370–7 (1987) provide examples of the preparation of the starting materials used in this method. The reduction of amides and urethanes to amines using lithium aluminium hydride is well known and there are many examples of this transformation in the chemical literature: for an example, see Journal of Heterocyclic Chemistry, Vol. 29, No. 6, pp. 1481–98 (1992). All the references provided above incorporated by reference into this document.

SUMMARY OF THE INVENTION

This invention relates to processes for the synthesis of various optically active amino pyrrolidinyl stereoisomers, or enantiomers, that may be attached to quinolonecarboxylic acids or naphthyridones or other appropriate compounds. Processes and essential intermediates are disclosed for the synthesis of compounds represented by the structure shown in figure $BG_5$, below.

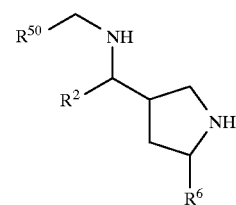

Figure $BG_5$ where $R^{50}$ is H, —($C_1$–$C_8$)alkyl, —($C_3$–$C_8$)cycloalkyl, —($C_1$–$C_8$)alkyl-($C_3$–$C_8$)cycloalkyl, —($C_6$–$C_{12}$ aryl), —($C_1$–$C_8$)alkyl-($C_6$–$C_{12}$ aryl), or the aryl or alkyl is substituted with one to three of the following groups, ($C_6$–$C_{12}$aryl), ($C_1$–$C_3$)alkyl, ($C_1$–$C_3$) alkoxy, halogen, trifluoromethyl, where $R^2$ is —$(C_1-C_8)$alkyl, —$(C_3-C_8)$cycloalkyl, —$(C_1-C_8)$alkyl-$(C_3-C_8)$cycloalkyl, —$(C_6-C_{12}$ aryl), —$(C_1-C_8)$alkyl-$(C_6-C_{12}$ aryl), or the aryl or alkyl is substituted with one to three of the following groups, $(C_6-C_{12}$ aryl), $(C_1-C_3)$alkyl, $(C_1-C_3)$ alkoxy, halogen, trifluoromethyl;

where $R^6$ is H, —$(C_1-C_8)$alkyl, —$(C_3-C_8)$cycloalkyl, —$(C_1-C_8)$alkyl-$(C_3-C_8)$cycloalkyl, —$(C_6-C_{12}$ aryl), —$(C_1-C_8)$alkyl-$(C_6-C_{12}$ aryl), or the aryl or alkyl is substituted with one to three of the following groups, —$(C_6-C_{12}$ aryl), —$(C_1-C_3)$alkyl, —$(C_1-C_3)$ alkoxy, halogen, trifluoromethyl;

Depending upon the starting materials used, compounds represented by the structure shown by figure $BG_5$ may have one of either of the two steriochemical arrangments shown by the structures below, figure $BG_{5-1}$,

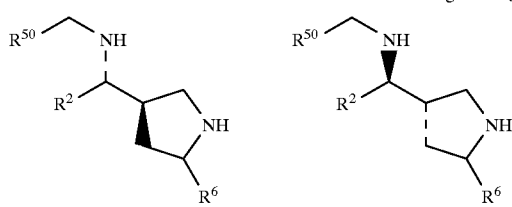

Figure $BG_{5-1}$ or, if the starting materials are a racemic mixture, the reaction may produce a 1:1 ratio of the combination of products shown in Figure $BG_{5-1}$, i.e. a racemic mixture.

This invention discloses two separate and distinct but related procedures for preparing the various enantiomers. Both procedures are significant advances in the art. The first group of procedures are described under the various reactions labeled as CHART A and CHART B reactions. The second major group of reactions are described under the various reactions labeled as CHART C, CHART D, CHART E and CHART F reactions.

The reactions from CHART A and CHART B are summarized below. This part of the invention comprises a series of reactions beginning with subjecting a compound or compounds represented by the structure shown in figure $AG_0$, below, Figure $AG_0$

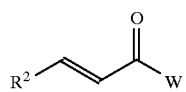

and W is Cl, Br, —$SR^2$ or figure to right,

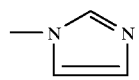

to treatment with $R^3XLi$
where $R^3$ is —$(C_1-C_8)$alkyl, —$(C_3-C_8)$cycloalkyl, —$(C_1-C_8)$alkyl-$(C_3-C_8)$cycloalkyl, —$(C_6-C_{12}$ aryl), —$(C_1-C_8)$alkyl-$(C_6-C_{12}$ aryl), or the aryl or alkyl is substituted with one to three of the following groups, —$(C_6-C_{12}$ aryl), —$(C_1-C_3)$alkyl, —$(C_1-C_3)$ alkoxy, halogen, trifluoromethyl,
and where X is O, NH, S,
to obtain a compound represented by the structure shown in figure $AG_{1(a)}$, below Figure $AG_{1(a)}$

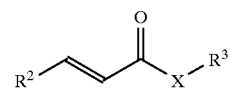

which is then reacted with a compound represented by the deprotonated form of the structure formed in figure $AG_{1(b)}$, below, or its appropriate isomer, Figure $AG_{1(b)}$

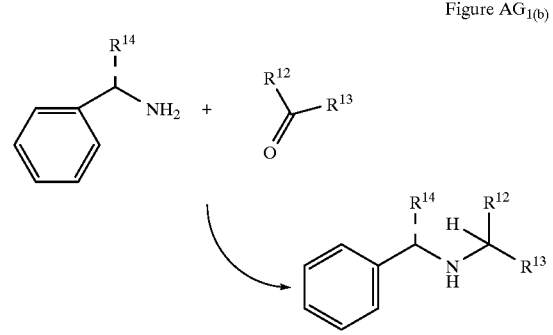

where $R^{12}$ is $(C_6-C_{12}$ aryl), or the aryl is substituted with one to three of the following groups, $(C_1-C_3)$alkyl, $(C_1-C_3)$ alkoxy, halogen, trifluoromethyl;

$R^{13}$ is H, —$(C_1-C_8)$alkyl, —$(C_3-C_8)$cycloalkyl, —$(C_1-C_8)$alkyl-$(C_3-C_8)$cycloalkyl, —$(C_6-C_{12}$ aryl), —$(C_1-C_8)$alkyl-$(C_6-C_{12}$ aryl), or the aryl or alkyl is substituted with one to three of the following groups, —$(C_6-C_{12}$ aryl), —$(C_1-C_3)$alkyl, —$(C_1-C_3)$ alkoxy, halogen, trifluoromethyl, where $R^{14}$ is —$(C_1-C_8)$alkyl, —$(C_3-C_8)$cycloalkyl, —$(C_1-C_8)$alkyl-$C_3-C_8)$cycloalkyl, —$(C_6-C_{12}$ aryl), —$(C_1-C_8)$alkyl-$(C_6-C_{12}$ aryl), or the aryl or alkyl is substituted with one to three of the following groups, —$(C_6-C_{12}$ aryl), —$(C_1-C_3)$alkyl, —$(C_1-C_3)$ alkoxy, halogen, trifluoromethyl;

to produce the compounds represented by the structures shown in figure $AG_2$, below, Figure $AG_2$

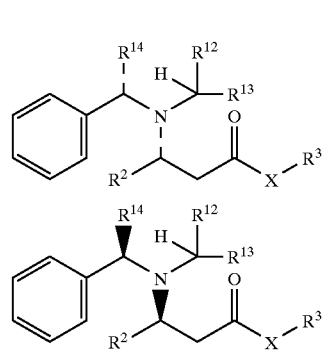

the compounds of figure $AG_2$ are then deprotected under hydrogenolysis conditions with a reducing agent such as Pearlman's catalyst, 10 percent palladium hydroxide on charcoal, to obtain the compounds, represented by the structures shown in figure $AG_3$, below, Figure AG₃

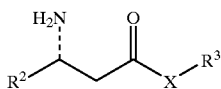 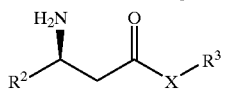

the compounds represented by the structure shown in figure AG₃ are then used according to the procedures described the reactions of CHART B to produce the desired compounds.

The reactions of CHART B comprises, using starting materials represented by the structure shown in figure $BG_{0-1}$, which are the same compounds represented by figure AG3, below, Figure $BG_{0-1}$

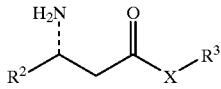 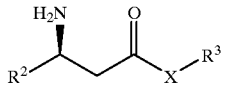

where $R^2$ and $R_3$ is —$(C_1-C_8)$alkyl, —$(C_3-C_8)$ cycloalkyl, —$(C_1-C_8)$alkyl-$(C_3-C_8)$cycloalkyl, —$(C_6-C_{12}$ aryl), —$(C_1-C_8)$alkyl-$(C_6-C_{12}$aryl), or the aryl or alkyl is substituted with one to three of the following groups, $(C_6-C_{12}$ aryl), $(C_1-C_3)$alkyl, $(C_1-C_3)$ alkoxy, halogen, trifluoromethyl;

X is O, NH, S reacting those starting materials with a compound represented by the structure in figure BG-R₁, below, Figure BG-R1

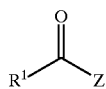

where $R^1$ is H, —$(C_1-C_8)$alkyl, —$(C_3-C_8)$cycloalkyl, —$(C_1-C_8)$alkyl-$(C_3-C_8)$cycloalkyl, —$(C_6-C_{12}$ aryl), —$(C_1-C_8)$alkyl-$(C_6-C_{12}$ aryl), —O—$(C_{1-8}$ alkyl), —O—$(C_{3-8}$ cycloalkyl), —O—$(C_{1-8}$ alkyl)$(C_{3-8}$ cycloalkyl), —O—$(C_{6-12}$ aryl), —O—$(C_{1-8}$ alkyl)-aryl, or the aryl or alkyl is substituted with one to three of the following groups, $(C_6-C_{12}$ aryl), $(C_1-C_3)$alkyl, $(C_1-C_3)$ alkoxy, halogen, trifluoromethyl, Z is Cl, N₃, S—$(C_6-C_{12})$aryl,

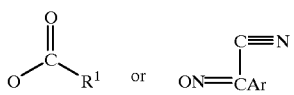

in a suitable organic solvent to yield a compound or compounds represented by the structure shown in figure $BG_{1-1}$, below, Figure $BG_{1-1}$

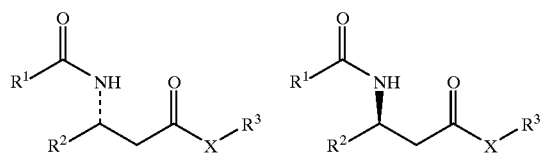

the compounds represented by BG₁ are dissolved in a suitable solvent, to which is added a compound represented by figure GRX, below, Figure GRX

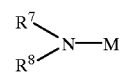

where $R^7$ and $R^8$ are defined independently and are —$(C_1-C_8)$alkyl, —$(C_3-C_8)$cycloalkyl, —$(C_1-C_8)$alkyl-$(C_6-C_{12})$aryl;

M is Li, Na, or K, the resulting dianion is then reacted with a compound represented by the structure shown in figure GYX, Figure GYX

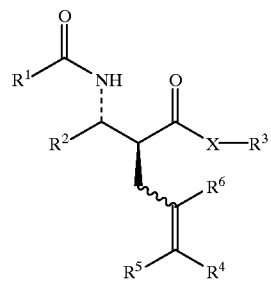

where, $R^4$, $R^5$ and $R^6$ are defined independently and are H, —$(C_1-C_8)$alkyl, —$(C_3-C_8)$cycloalkyl, —$(C_1-C_8)$alkyl-$(C_3-C_8)$cycloalkyl, —$(C_6-C_{12}$ aryl), —$(C_1-C_8)$alkyl-$(C_6-C_{12}$ aryl), or the aryl or alkyl is substituted with one to three of the following groups, —$(C_6-C_{12}$ aryl), —$(C_1-C_3)$ alkyl, —$(C_1-C_3)$ alkoxy, halogen, trifluoromethyl;

Y is halogen, —OTs, —OMs, or —OTf to produce a compound or compounds represented by figure $BG_{2-1}$ Figure $BG_{2-1}$

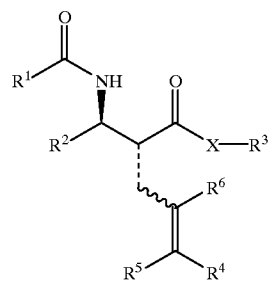

the compound or compounds represented by the structures in figure $BG_{2-1}$ are then used according to the process described below for the preparation of a compound or compounds represented by the structures on the left side, or the right side of figure $BG_{4-1}$, below, or, if the starting materials are a racemic mixture, the reaction may produce a mixed ratio of compounds represented on both sides of the figure $BG_{4-1}$, below,

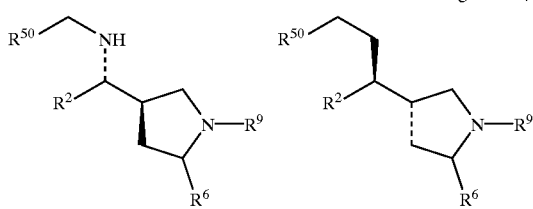

Figure BG$_{4-1}$ where R$^{50}$ is H, —(C$_1$–C$_8$)alkyl, —(C$_3$–C$_8$)cycloalkyl, —(C$_1$–C$_8$)alkyl-(C$_3$–C$_8$)cycloalkyl, —(C$_6$–C$_{12}$ aryl), —(C$_1$–C$_8$)alkyl-(C$_6$–C$_{12}$ aryl), or the aryl or alkyl is substituted with one to three of the following groups, (C$_6$–C$_{12}$ aryl), (C$_1$–C$_3$)alkyl, (C$_1$–C$_3$) alkoxy, halogen, trifluoromethyl. When R$^1$ is —O—(C$_{1\text{-}8}$ alkyl), —O—(C$_{3\text{-}8}$ cycloalkyl), —O—(C$_{1\text{-}8}$ alkyl)(C$_{3\text{-}8}$ cycloalkyl), —O—(C$_{6\text{-}12}$ aryl), —O—(C$_{1\text{-}8}$ alkyl)-aryl, then reduction with LAH, DIBAL or Borane will always produce R$^{50}$ is H.

where R$^2$ is —(C$_1$–C$_8$)alkyl, —(C$_3$–C$_8$)cycloalkyl, —(C$_1$–C$_8$)alkyl-(C$_3$–C$_8$)cycloalkyl, —(C$_6$–C$_{12}$ aryl), —(C$_1$–C$_8$)alkyl-(C$_6$–C$_{12}$ aryl), or the aryl or alkyl is substituted with one to three of the following groups, (C$_6$–C$_{12}$ aryl), (C$_1$–C$_3$)alkyl, (C$_1$–C$_3$) alkoxy, halogen, trifluoromethyl;

(C$_6$–C$_{12}$) aryl, where R$^6$ is H, —(C$_1$–C$_8$)alkyl, —(C$_3$–C$_8$)cycloalkyl, —(C$_1$–C$_8$)alkyl-(C$_3$–C$_8$)cycloalkyl, —(C$_6$–C$_{12}$ aryl), —(C$_1$–C$_8$)alkyl-(C$_6$–C$_{12}$ aryl), or the aryl or alkyl is substituted with one to three of the following groups, —(C$_6$–C$_{12}$ aryl), —(C$_1$–C$_3$)alkyl, —(C$_1$–C$_3$) alkoxy, halogen, trifluoromethyl;

where R$^9$ is H, —(C$_1$–C$_8$)alkyl, —(C$_3$–C$_8$)cycloalkyl, —(C$_1$–C$_8$)alkyl-(C$_3$–C$_8$)cycloalkyl, —(C$_6$–C$_{12}$ aryl), —(C$_1$–C$_8$)alkyl-(C$_6$–C$_{12}$ aryl), or the aryl or alkyl is substituted with one to three of the following groups, —(C$_6$–C$_{12}$ aryl), —(C$_1$–C$_3$)alkyl, —(C$_1$–C$_3$) alkoxy, halogen, trifluoromethyl;

comprising treating a compound or compounds represented by figure BG$_{3-1}$ with a reducing agent such as with LiAlH$_4$, DIBAL or Borane in a suitable solvent such as THF preceeded by the following process, a process for preparing a compound or compounds represented by figure BG$_{3-1}$,

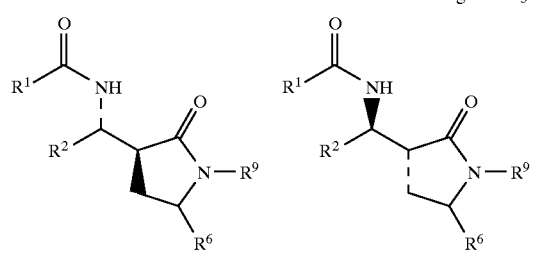

Figure BG$_{3-1}$ where R$^1$ is H, —(C$_1$–C$_8$)alkyl, —(C$_3$–C$_8$)cycloalkyl, —(C$_1$–C$_8$)alkyl-(C$_3$–C$_8$)cycloalkyl, —(C$_6$–C$_{12}$ aryl), —(C$_1$–C$_8$)alkyl-(C$_6$–C$_{12}$ aryl), —O—(C$_{1\text{-}8}$ alkyl), —O—(C$_{3\text{-}8}$ cycloalkyl), —O—(C$_{1\text{-}8}$ alkyl)(C$_{3\text{-}8}$ cycloalkyl), —O—(C$_{6\text{-}12}$ aryl), —O—(C$_{1\text{-}8}$ alkyl)-aryl, or the aryl or alkyl is substituted with one to three of the following groups, (C$_6$–C$_{12}$ aryl), (C$_1$–C$_3$)alkyl, (C$_1$–C$_3$) alkoxy, halogen, trifluoromethyl, where R$^2$ is —(C$_1$–C$_8$)alkyl, —(C$_3$–C$_8$)cycloalkyl, —(C$_1$–C$_8$)alkyl-(C$_3$–C$_8$)cycloalkyl, —(C$_6$–C$_{12}$ aryl), —(C$_1$–C$_8$)alkyl-(C$_6$–C$_{12}$ aryl), or the aryl or alkyl is substituted with one to three of the following groups, (C$_6$–C$_{12}$ aryl), (C$_1$–C$_3$)alkyl, (C$_1$–C$_3$) alkoxy, halogen, trifluoromethyl;

where R$^6$ is H, —(C$_1$–C$_8$)alkyl, —(C$_3$–C$_8$)cycloalkyl, —(C$_1$–C$_8$)alkyl-(C$_3$–C$_8$)cycloalkyl, —(C$_6$–C$_{12}$ aryl), —(C$_1$–C$_8$)alkyl-(C$_6$–C$_{12}$ aryl), or the aryl or alkyl is substituted with one to three of the following groups, —(C$_6$–C$_{12}$ aryl), —(C$_1$–C$_3$)alkyl, —(C$_1$–C$_3$) alkoxy, halogen, trifluoromethyl;

where R$^9$ is H, —(C$_1$–C$_8$)alkyl, —(C$_3$–C$_8$)cycloalkyl, —(C$_1$–C$_8$)alkyl-(C$_3$–C$_8$)cycloalkyl, —(C$_6$–C$_{12}$ aryl), —(C$_1$–C$_8$)alkyl-(C$_6$–C$_{12}$ aryl), or the aryl or alkyl is substituted with one to three of the following groups, —(C$_6$–C$_{12}$ aryl), —(C$_1$–C$_3$)alkyl, —(C$_1$–C$_3$) alkoxy, halogen, trifluoromethyl;

which comprises subjecting to ozonolysis a compound or compounds represented by figure BG$_{2-1}$

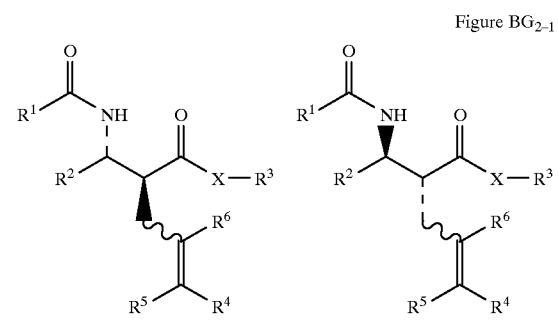

Figure BG$_{2-1}$ where R$^3$ is —(C$_1$–C$_8$)alkyl, —(C$_3$–C$_8$)cycloalkyl, —(C$_1$–C$_8$)alkyl-(C$_3$–C$_8$)cycloalkyl, —(C$_6$–C$_{12}$ aryl), —(C$_1$–C$_8$)alkyl-(C$_6$–C$_{12}$ aryl), or the aryl or alkyl is substituted with one to three of the following groups, —(C$_6$–C$_{12}$ aryl), —(C$_1$–C$_3$)alkyl, —(C$_1$–C$_3$) alkoxy, halogen, trifluoromethyl, R$^4$, R$^5$ and R$^6$ are defined previously, X is O, NH, or S, followed by reaction with R$^9$—NH$_2$, under reducing conditions, such as with sodium cyano borohydride, sodium triacetoxy borohydride or sodium borohydride, (in order of preference) at 0°–50° C., or a cool temperature to control heat, to produce the desired compounds.

The invention also comprises the reactions of CHARTS C and D, summarized below. The process for the preparation of a compound or of compounds represented by the structures on the left side, or the right side of figure CG$_3$, below, or, if the starting materials are a racemic mixture, the reaction may produce a mixed ratio of compounds represented on both sides of the figure CG$_3$, below,

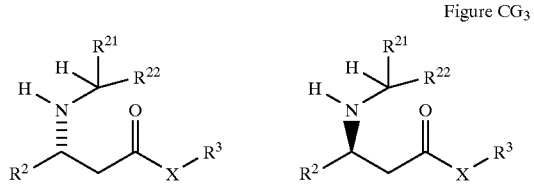

Figure CG$_3$ which comprises, a series of reactions, beginning with an appropriate optically active amine represented by figure CG-R$_1$, below, Figure CG-R₁

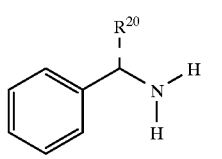 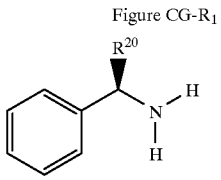

where $R^{20}$ is —$(C_1$–$C_8)$alkyl, —$(C_3$–$C_8)$cycloalkyl, —$(C_1$–$C_8)$alkyl-$(C_3$–$C_8)$cycloalkyl, —$(C_6$–$C_{12}$ aryl), —$(C_1$–$C_8)$alkyl-$(C_6$–$C_{12}$ aryl), or the aryl or alkyl is substituted with one to three of the following groups, —$(C_6$–$C_{12}$ aryl), —$(C_1$–$C_3)$alkyl, —$(C_1$–$C_3)$ alkoxy, halogen, trifluoromethyl, is condensed with a carbonyl compound, such as one represented by the structure shown in Figure CG-R₂ below, Figure CG-R₂

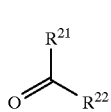

where $R^{21}$ and $R^{22}$ are defined independently and are H, —$(C_1$–$C_8)$alkyl, —$(C_3$–$C_8)$cycloalkyl, —$(C_1$–$C_8)$alkyl-$(C_3$–$C_8)$cycloalkyl, —$(C_6$–$C_{12}$ aryl), —$(C_1$–$C_8)$alkyl-$(C_6$–$C_{12}$ aryl), or the aryl or alkyl is substituted with one to three of the following groups, —$(C_6$–$C_{12}$ aryl), —$(C_1$–$C_3)$ alkyl, —$(C_1$–$C_3)$ alkoxy, halogen, trifluoromethyl; under reducing conditions using NaBH₄ or a similar suitable boron hydride reducing agent in a suitable solvent such as THF to obtain compounds represented by the structures shown in figure $CG_{1(b)}$ below, Figure CG₁(b)

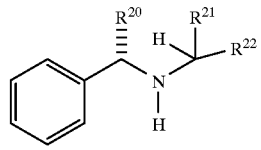 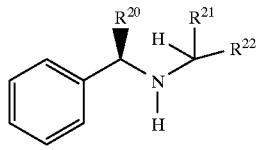

compounds represented by the deprotonated form of figures $CG_{1(b)}$, above, then undergoes a Michael Addition reaction with a compound represented by the structure shown in Figure $CG_{1(a)}$, below, A compound represented by the structures shown in $CG_{1(a)}$, below,

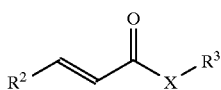

where, $R^2$ and $R^3$ are independently, lower alkyl, alkylaryl, or optionally substituted aryl, then deprotonation is carried out with an appropriate base such as n-BuLi, to produce compounds, after coupling, represented by the structures shown in figure CG₂ below, Figure CG₂

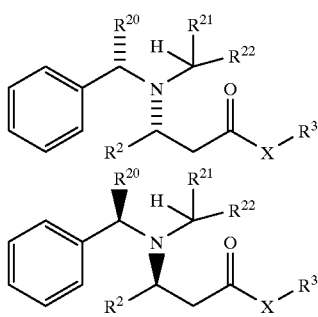

the carbon nitrogen bonds are hydrogenolytically cleaved with an appropriate reducing agent such as Pearlman's catalyst, 20 percent palladium hydroxide on charcoal, in an appropriate solvent, such as EtOH, to obtain the desired compounds. Products of the reactions of CHART C are then used in the reactions of CHART D, summarized below. Note that the compounds represented by figure CG₃ are the same as those represented by figure DG₀.

The process for the preparation of a compound or the compounds represented by the structures on the left side, or the right side of figure DG₇, below, or, if the starting materials are a racemic mixture, the reaction may produce a mixed ratio of compounds represented on both sides of the figure DG₇, below, Figure DG₇

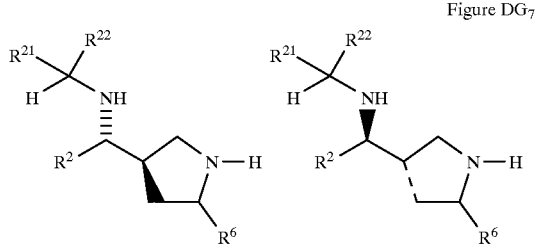

which comprises a series of reactions, the reactions beginning with a compound represented by the structures in figures DG₀, below, Figure DG₀

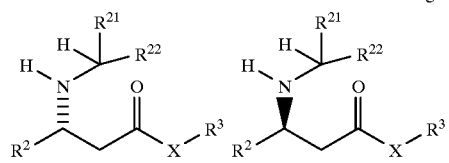

where $R^2$ and $R^3$ are defined independently and are lower alkyl, alkylaryl, or optionally substituted aryl; where $R^{21}$ and $R^{22}$ are defined independently and are H, —$(C_1$–$C_8)$ alkyl, —$(C_3$–$C_8)$cycloalkyl, —$(C_1$–$C_8)$alkyl-$(C_3$–$C_8)$ cycloalkyl, —$(C_6$–$C_{12}$ arly), —$(C_1$–$C_8)$alkyl-$(C_6$–$C_{12}$ aryl), or the aryl or alkyl is substituted with one to three of the following groups, —$(C_6$–$C_{12}$ aryl), —$(C_1$–$C_3)$alkyl, —$(C_1$–$C_3)$ alkoxy, halogen, trifluoromethyl; and where X is O, NH, S; are dissolved in a suitable organic solvent such as tetrahydrofuran, and then added, in a cool temperature to control exothermic formations under an inert atmosphere, such as between a temperature of –50° C. and 0° C. in a nitrogen atmosphere, to a solution of a compound of the description in figure GRX, dissolved in a suitable organic solvent, Figure GRX

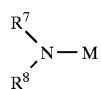

where $R^7$ and $R^8$ are defined independently and are —$(C_1$–$C_8)$alkyl, —$(C_3$–$C_8)$cycloalkyl, —$(C_1$–$C_8)$alkyl-$(C_6$–$C_{12})$aryl; where M is Li, Na, or K; and the resulting anion or dianion is then reacted with a compound represented by the structure shown in figure DG-$R_2$ below, Figure DG-$R_2$

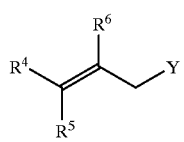

where $R^4$, $R^5$, and $R^6$ are independent and are H, alkyl, alkylaryl, or optionally substituted aryl, and where Y is halogen, —OTs, —OMs, or —OTf; to obtain a compound represented by the structures shown in figure $DG_1$, below.

Figure $DG_1$

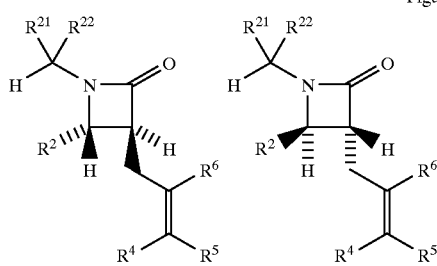

the compounds represented by the structures shown in figure $DG_1$ are subjected to an established method of ozonolysis, such as bubbling $O_3$ from an ozone generator, such as a Welsbach ozonator, through the reaction mixture in an appropriate solvent, such as water or methanol, followed by reduction of the intermediate ozonide with an appropriate boron hydride reducing agent such as $NaBH_4$ or $LiBH_4$ to obtain a compound represented by the structures shown in figure $DG_2$, below, Figure $DG_2$

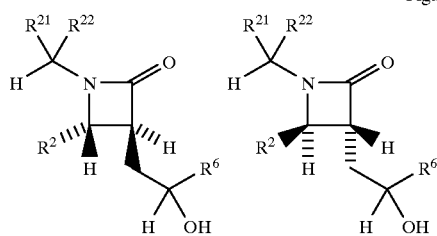

the compounds represented by the structures shown in figure $DG_2$ are treated with an appropriate amine base, such as triethylamine, and an activating agent, such as methanesulfonyl chloride in a solvent such as tetrahydrofuran or toluene to obtain a compound represented by the structures shown in figure $DG_3$, below, Figure $DG_3$

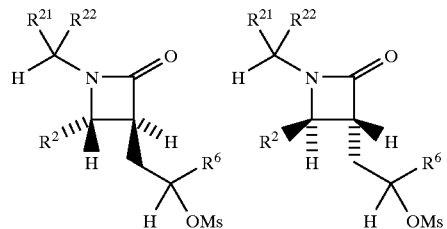

where Ms is mesylate, the compounds represented by the structures shown in figure $DG_3$ are treated in an appropriate solvent such as toluene or THF with an amine represented by the structure shown in figure DG-$R_1$ below, Figure DG-$R_1$

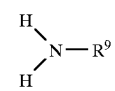

where $R^9$ is H, —$(C_1$–$C_8)$alkyl, —$(C_3$–$C_8)$cycloalkyl, —$(C_1$–$C_8)$alkyl-$(C_3$–$C_8)$cycloalkyl, —$(C_6$–$C_{12}$ aryl), —$(C_1$–$C_8)$alkyl-$(C_6$–$C_{12}$ aryl), or the aryl or alkyl is substituted with one to three of the following groups, —$(C_6$–$C_{12}$ aryl), —$(C_1$–$C_3)$alkyl, —$(C_1$–$C_3)$ alkoxy, halogen, trifluoromethyl; to obtain a compound represented by the structures shown in figure $DG_4$ below, Figure $DG_4$

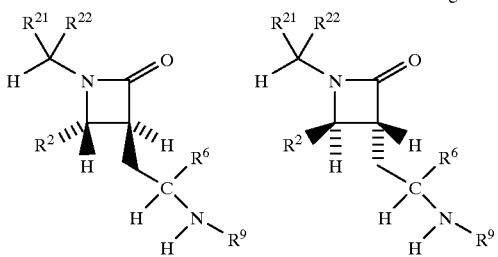

the compounds represented by the structures shown in figure $DG_4$ undergo thermal isomerization to give a compound represented by the structures shown in figure $DG_5$, below, Figure $DG_5$

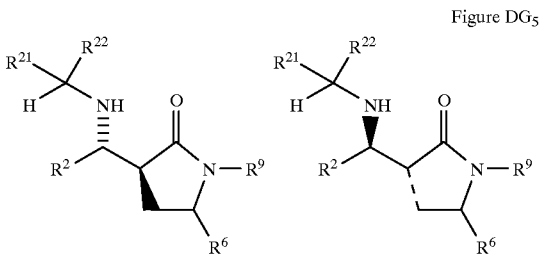

the compounds represented by the structures shown in figure $DG_5$ are treated with a suitable reducing agent such as $LiAlH_4$, DIBAL or borane in a suitable solvent such as THF to obtain a compound represented by the structures shown in figure $DG_6$, below, Figure DG₆

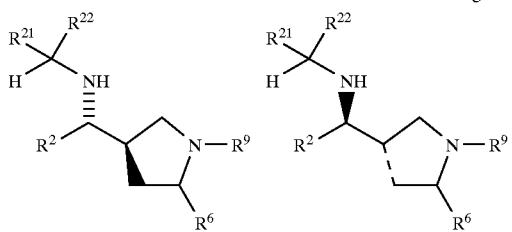

when R⁹ is a protective group, where, for example, an alkylaryl is connected to the nitrogen atom with one carbon atom between the nitrogen and the aryl, then the compounds represented by the structures shown in figure DG₆ may be hydrogenolytically cleaved with, for example, 20 percent palladium hydroxide on charcoal, H₂ to obtain the desired compound or compounds.

Another series of reactions, similar to those in CHART C and CHART D are also claimed in this invention, those are from the reactions of CHART E and CHART F, below.

Also claimed is a process for the preparation of compounds represented by the structures on the left side, or the right side of figure FG₆, below, or, if the starting materials are a racemic mixture, the reaction may produce a mixed ratio of compounds represented on both sides of the figure FG₆, below, Figure FG₆

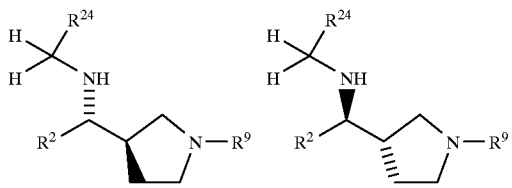

which comprises a series of reactions, the reactions beginning with a compound represented by the structures in figures EG-R₁, below, Figure EG-R₁

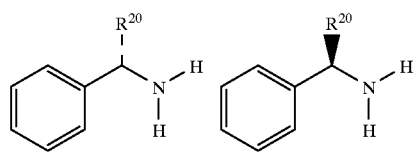

where $R^{20}$ is —$(C_1-C_8)$alkyl, —$(C_3-C_8)$cycloalkyl, —$(C_1-C_8)$alkyl-$(C_3-C_8)$cycloalkyl, —$(C_6-C_{12}$ aryl), —$(C_1-C_8)$alkyl-$(C_6-C_{12}$ aryl), or the aryl or alkyl is substituted with one to three of the following groups, —$(C_6-C_{12}$ aryl), —$(C_1-C_3)$alkyl, —$(C_1-C_3)$ alkoxy, halogen, trifluoromethyl; is condensed with a compound represented by the structure shown in figure EG-R₂ below, Figure EG-R₂

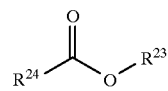

where $R^{23}$ is —$(C_1-C_8)$alkyl, —$(C_3-C_8)$cycloalkyl, —$(C_1-C_8)$alkyl-$(C_3-C_8)$cycloalkyl, —$(C_6-C_{12}$ aryl), —$(C_1-C_8)$alkyl-$(C_6-C_{12}$ aryl), or the aryl or alkyl is substituted with one to three of the following groups, —$(C_6-C_{12}$ aryl), —$(C_1-C_3)$alkyl, —$(C_1-C_3)$ alkoxy, halogen, trifluoromethyl;

where $R^{24}$ is H, —$(C_1-C_8)$alkyl, —$(C_3-C_8)$cycloalkyl, —$(C_1-C_8)$alkyl-$(C_3-C_8)$cycloalkyl, —$(C_6-C_{12}$ aryl), —$(C_1-C_8)$alkyl-$(C_6-C_{12}$ aryl), or the aryl or alkyl is substituted with one to three of the following groups, —$(C_6-C_{12}$ aryl), —$(C_1-C_3)$alkyl, —$(C_1-C_3)$ alkoxy, halogen, trifluoromethyl;

to obtain a compound represented by the structures shown in Figure EG$_{1(b')}$ below, Figure EG$_{1(b')}$

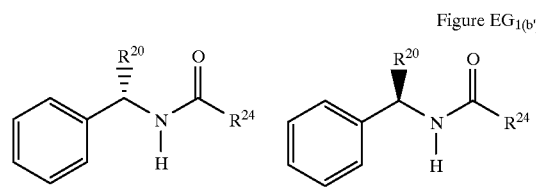

which is treated with an appropriate reducing agent such as LiAlH₄, DIBAL or Borane in a suitable solvent such as THF to obtain compounds represented by the structures shown in figure EG$_{1(b)}$, below.

Figure EG$_{1(b)}$

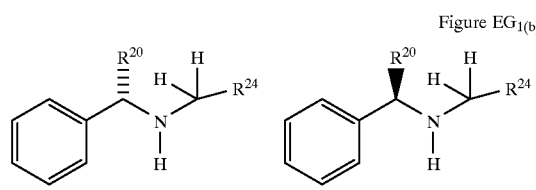

the compounds represented by the structures shown in EG$_{1(a)}$, below,

Figure EG$_{1(a)}$

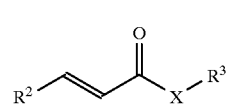

where $R^2$ are $R^3$ are independently, lower alkyl, arlkylaryl, or optionally substituted aryl, then undergoes a Michael Addition reaction with a compound represented by the deprotonated form of the structures shown in figure EG$_{1(b)}$, (the deprotonation is carried out with an appropriate base such as n-BuLi) to produce compounds, after coupling, represented by the structures shown in figure EG₂, below, Figure EG₂

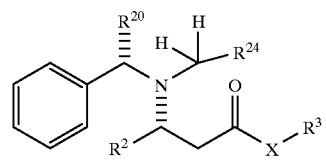

-continued

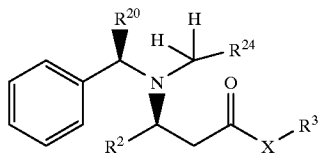

the compounds represented by the structures shown in figure EG$_2$ have carbon nitrogen bonds that are hydrogenolytically cleaved with an appropriate reducing agent such as Pearlman's catalyst, 20 percent palladium hydroxide on charcoal, in an appropriate solvent, such as EtOH, to obtain the compounds represented by the structures shown in figure EG$_3$, same figure as FG$_0$, below,

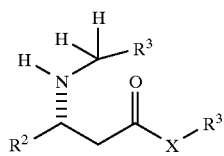

Figure EG$_3$ = Figure FG$_0$ where R$^2$, R$^3$, R$^{24}$ and X are defined above); is dissolved in a suitable organic solvent such as tetrahydrofuran, and added, in a cool temperature to control exothermic formations under an inert atmosphere, such as, between a temperature of −50° C. and 0° C. in a nitrogen atmosphere, to a solution of a compound represented by the structures shown in figure GRX, below, Figure GRX

where R$^7$ and R$^8$ are defined independently and are —(C$_1$–C$_8$)alkyl, —(C$_3$–C$_8$)cycloalkyl, —(C$_1$–C$_8$)alkyl-(C$_6$–C$_{12}$)aryl; and M is Li, Na, or K; the resulting anion or dianion is then reacted with a compound represented by the structures shown in figure FG-R$_2$, below, Figure FG-R$_2$

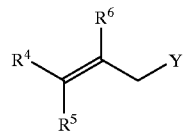

where R$^4$, R$^5$, and R$^6$ are independent and are H, alkyl, alkylaryl, or optionally substituted aryl, and where Y is halogen, —OTs, —OMs, or —OTf; to obtain a compound represented by the structures shown in figure FG$_1$, below, Figure FG$_1$

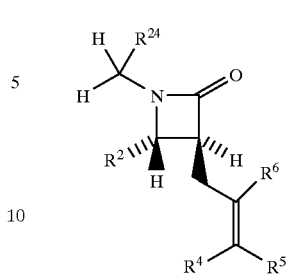 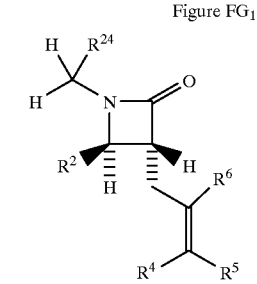

the compounds represented by the structures shown in figure FG$_1$ are subjected to an established method of ozonolysis, such as bubbling O$_3$ from an ozone generator, such as a Welsbach ozonator, through the reaction mixture in an appropriate solvent such as water or methanol, followed by treatment of the intermediate ozonide with an appropriate boron hydride reducing agent such as NaBH$_4$ or LiBH$_4$ to obtain a compound represented by the structures shown in figure FG$_2$, below, Figure FG$_2$

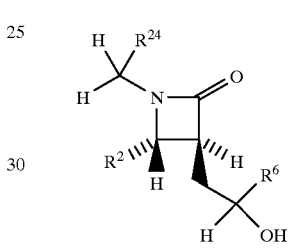 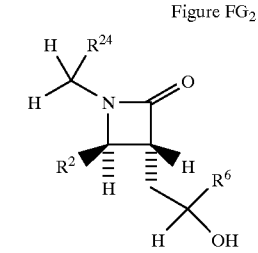

the compounds represented by the structures shown in figure FG$_2$ are treated with an appropriate amine base, such as triethylamine, and methanesulfonyl chloride in a solvent such as tetrahydrofuran or toluene to obtain a compound represented by the structures shown in figure FG$_3$, below, Figure FG$_3$

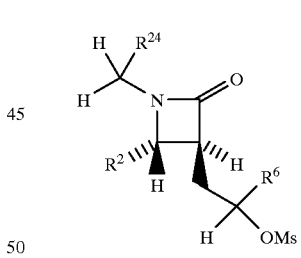 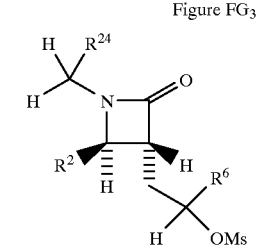

the compound or compounds represented by the structures shown in figure FG$_3$, where Ms is mesylate, are treated in an appropriate solvent such as toluene or THF with an amine represented by the structure shown in figure FG-R$_1$ below, Figure FG-R$_1$

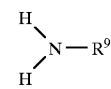

where R$^9$ is H, —(C$_1$–C$_8$)alkyl, —(C$_3$–C$_8$)cycloalkyl, —(C$_1$–C$_8$)alkyl-(C$_3$–C$_8$)cycloalkyl, —(C$_6$–C$_{12}$ aryl), —(C$_1$–C$_8$)alkyl-(C$_6$–C$_{12}$ aryl), or the aryl or alkyl is substituted with one to three of the following groups, —(C$_6$–C$_{12}$ aryl), —(C$_1$–C$_3$)alkyl, —(C$_1$–C$_3$) alkoxy, halogen, trifluoromethyl; to obtain a compound represented by the structures shown in figure FG$_4$ below,

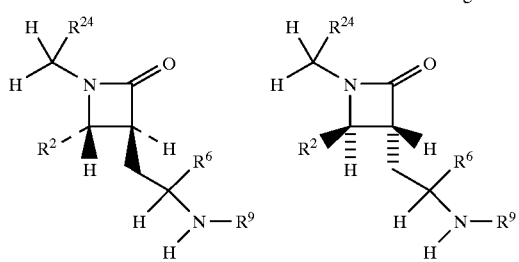

Figure FG$_4$ the compounds represented by the structures shown in figure FG$_4$ thermally isomerizes to give a compound represented by the structures shown in figure FG$_5$ below,

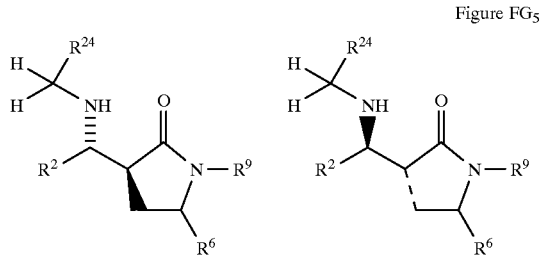

Figure FG$_5$ the compound or compounds represented by the structures shown in figure FG$_5$ are treated with a suitable reducing agent such as LiAlH$_4$, DIBAL or Borane in a suitable solvent such as THF to obtain the desired compounds.

These reactions and processes are of course designed to be used with specific reactants to produce specific products same of these specific reactions and products are described more completely herein.

DETAILED DESCRIPTION OF THE INVENTION

The compounds of this invention are identified by both descriptive names and by reference to structures shown in appropriate charts and text. In appropriate situations, the proper stereochemistry, an important aspect of this invention is also represented in the charts.

The compounds and processes of this invention may be divided into two groups. The four groups are described in CHARTs A, and B. Within each group the reactions are shown as steps. CHARTs AG and BG are generic charts, various substituted R groups are indicated. The steps from CHARTs AG and BG are generic steps that describe reactions that are specified to the degree needed to enable one ordinarily skilled in the art to practice the invention. Following the general procedures for each group are one or more detailed preparations and examples that describe precisely how to prepare specific compounds of this invention. CHART AX1 thus describes the experimental steps for one specific reaction sequence described in CHART AG and BX1 shows a specific reaction from CHART BG. Note that the generic charts as well as the specific reactions show the stereochemistry of the compounds. The specific procedures are to be construed as merely illustrative, and do not impose limitations upon the general reaction schemes in any manner whatsoever. Those skilled in the art will promptly recognize appropriate variations from the procedures both as to reactants as well as to reaction conditions and techniques.

DEFINITIONS

The following words or abbreviations are used to describe this invention. The definitions and examples provided below are intended to provide guidance and illustration for procedures and methods described herein but are not intended to impose limitations upon the subject matter described.

Variables defined.

In this document the parenthetical term ($C_n$–$C_m$) is inclusive such that a compound of ($C_1$–$C_8$) would include compounds of one to 8 carbons and their isomeric forms. The various carbon moieties are defined as follows:

Alkyl refers to an aliphatic hydrocarbon radical and includes branched or unbranched forms such as methyl, ethyl, n-propyl, isopropyl, n-butyl, isobutyl, sec-butyl, t-butyl, n-pentyl, isopentyl, n-hexyl, isohexyl, n-heptyl, isoheptyl, and n-octyl, etc.

Lower alkyl refers to alkyl compounds that includes 1 to 8 carbons, $C_1$–$C_8$ and their isomeric forms.

Alkoxy, as represented by —OR$_x$ when R$_x$ is a ($C_1$–$C_8$) alkyl, refers to an alkyl radical which is attached to the remainder of the molecule by oxygen and includes branched or unbranched forms such as methoxy, ethoxy, n-propoxy, isopropoxy, n-butoxy, isobutoxy, sec-butoxy, t-butoxy, n-pentoxy, isopentoxy, n-hexoxy, isohexoxy, n-heptoxy, isoheptoxy, and n-octoxy.

Aryl refers to aromatic hydrocarbon radicals that contain 6 to 12 carbon atoms such as phenyl, α-naphthyl, β-naphthyl, m-methylphenyl, p-trifluoromethylphenyl and the like. The aryl groups can also be substituted with one to three of any of the following groups: $C_1$–$C_3$ alkoxy, $C_1$–$C_3$ alkyl, trifluoromethyl, halogen.

Alkylaryl refers to an alkyl, as defined above, attached to an aryl, as defined above. A moiety expressed as "lower alkylaryl" could also be expressed as "($C_1$–$C_8$)alkylaryl" the alkyl portion would be attached to the molecule of interest. Benzyl for example would be an unsubstituted $C_1$alkylaryl.

Aryloxy refers to an aryl radical, as described above, which is attached to the remainder of the molecule by oxygen.

Arylalkoxy refers to an aryl radical, as described above, which is attached to an alkyl, as described above, which is attached to the remainder of the molecule by oxygen.

Cycloalkyl refers to a radical of a saturated cyclic hydrocarbon containing 3 to 10 carbon atoms, ($C_3$–$C_{10}$) cycloalkyl, such as cyclopropyl, cyclobutyl, cyclopentyl, cyclohexyl, cycloheptyl, cyclooctyl, cyclononyl and cyclodecyl. The term also includes alkyl-substituted cycloalkyl, such as 2-methylcyclopropyl, 2,2-dimethylcyclopropyl, 2,3 diethylcyclopropyl, 2-butylcyclopropyl, cyclobutyl, 2-methylcyclobutyl, 3-propylcyclobutyl, 2,2-dimethylcyclopentyl.

Cycloalkoxy refers to a cycloalkyl, as described above, which is attached to the remainder of the molecule by oxygen.

Halogen or Halo refers to the halogens which include fluorine, chlorine, bromine and iodide.

Constants defined.

BnO is benzyloxy. DIBAL is Diisobutyl Aluminum Hydride. Borane may refer to any borane, BH$_3$, and related reagents such as diborane, B$_2$H$_6$. Boron hydride reducing agents are exemplified by such reagents as LiBH$_4$ and NaBH$_4$. ° C. is degree Centigrade. Celite or Celite Pad is commercially available filter aid. Et$_2$O is diethyl ether. EtOAc is ethyl acetate. g is gram. H$_2$ is hydrogen gas. Hx is hexane. HCl-Hydrochloric acid. i-Pr₂NH is diisopropylamine. L is liter. LAH or LiAlH₄ is Lithium Aluminum Hydride. LDA is Lithium Diisopropyl Amide. M is Molar. Mol. is mole. mg is milligram. MgSO₄ is Magnesium Sulphate. min. is minute. mL is milliliter. mM is milliMole. Ms is mesylate. N is Normality of solution, where appropriate. N is Nitrogen atom where appropriate, N₂ is nitrogen gas or atmosphere. N₃ is azide or azido or azido carboxy compound. NMR is Nuclear Magnetic Resonance. NaOH is Sodium Hydroxide. NaCNBH₃ is Sodium Cyano Borohydride. O is Oxygen. OEt is ethoxy. —OMs is methylsulfonate or mesylate. —OTf is trifluoromethylsulfonate or triflate. —OTs is p-toluenesulfonate or tosylate. "Pearlman's" catalyst is 10 percent Paladium Hydroxide on charcoal. psi is pounds per square inch. n-BuLi is n-Butyllithium. RT or R.T. is room temperature. S is Sulphur. S-aryl is a thioaryl compound. SiO₂ is Silica gel. Strong hydride reducing agents are exemplified by such reagents as DIBAL, LAH, and Borane. t-BuOH is tertiary butyl alcohol. THF is tetrahydrofuran. "Welsbach ozonator" is an example of an ozone generating device. Any suitable ozone generating device may be used in the operation of this invention.

Temperature and atmosphere considerations. Many reactions in this invention are performed under cooler conditions to better cope with heat generated during the reaction (exothermic formations). The deprotonation reactions are typical of this type of exothermic reaction. These deprotonation reactions are usually run at 0 to −50° C., this is the preferred range using the reactants used here. This is not to say that the reaction must be run at this range, indeed, many of the deprotection reactions could be run anywhere from room temperature down to below −100° C. When the atmosphere is described it is intended to provide a preferred method of running the reaction. The Michael Addition reactions, among others, have fewer side reactions when they are run under an atmosphere that excludes water. Thus reactions run under nitrogen gas could also be run under argon gas or other suitable inert or nonreactive gases that would operate to exclude side reactions with water. The Michael Addition reactions also have greater selectivity when they are run at lower temperatures. Thus the preferred range for a Michael Addition is about −70 to −80° C., but this reaction can be run from room temperature to below −100° C., but the selectivity declines appreciably at higher temperatures.

The best mode of performing the reactions appears to be according to the procedures found in CHARTS E and CHARTS F.

The Reactions and Compounds of the Charts

The reactions of this invention are grouped in varous CHARTS. The CHARTS are logical groupings of sequential reactions. The word CHART indicates the written procedures, including what is commonly known in the art and obvious variants thereof, as well as the specific flow charts containing images or drawings suggesting chemical structures. Sometimes the product of the reactions in one CHART will be used as the starting material for the reaction in another CHART. In this manner CHARTS A and B are related, CHARTS C and D are related, and CHARTS E and F are related. CHARTS A, C and E describe three different procedures for making similar compounds, as do CHARTS B, D, and E. The CHARTS are named sequentially by the letters A–E, the letter "G" in the CHART indicates the CHART shows a general scheme, with structures containing variables. The letter "X" in the name of the CHART indicates it is a specific reaction with X meaning an specific embodiment or example. Thus CHART AG shows generically how to make many compounds, the products of this CHART could be used as starting material for CHART BG and representational embodiments are shown in CHARTS AX1, AX2, BX1, BX2, etc.

The Reactions and Compounds of Chart A

CHART AG shows the general reaction scheme and the major reaction Steps of the reactions involved in the synthesis of the compounds of CHART A. CHART AX1 shows a specific reaction scheme for a single specific compound that is generally described in CHART A. The final compounds produced by the descriptions for CHART A are used as the starting materials for the reactions of CHART B. A description of the Steps and procedures from the compounds and reactions shown in CHARTs AG and AX1 appear below, followed by CHART AG and CHART AX1. The reactions and compounds of CHART B follows this section.

The Steps of Chart AG

The starting materials utilized to prepare the compounds of this invention are either available commercially or can be prepared by the following methods.

Step 1(a). $AG_0 \rightarrow AG_{1(a)}$.

A compound represented by the structure shown in figure $AG_0$, below

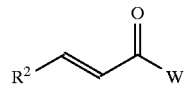

Figure AG₀ where $R^2$ is —($C_1$–$C_8$)alkyl, —($C_3$–$C_8$)cycloalkyl, —($C_1$–$C_8$)alkyl-($C_3$–$C_8$)cycloalkyl, —($C_6$–$C_{12}$ aryl), —($C_1$–$C_8$)alkyl-($C_6$–$C_{12}$ aryl), or the aryl or alkyl is substituted with one to three of the following groups, —($C_6$–$C_{12}$ aryl), —($C_1$–$C_3$)alkyl, ($C_1$–$C_3$) alkoxy, halogen, trifluoromethyl;

and W is Cl, Br, —$SR^2$ or

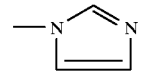

is treated with $R^3XLi$ where $R^3$ is —($C_1$–$C_8$)alkyl, —($C_3$–$C_8$)cycloalkyl, —($C_1$–$C_8$)alkyl-($C_3$–$C_8$)cycloalkyl, —($C_6$–$C_{12}$ aryl), —($C_1$–$C_8$)alkyl-($C_6$–$C_{12}$ aryl), or the aryl or alkyl is substituted with one to three of the following groups, —($C_6$–$C_{12}$ aryl), —($C_1$–$C_3$)alkyl, —($C_1$–$C_3$) alkoxy, halogen, trifluoromethyl; and X is O, NH, S, to obtain a compound represented by the structure shown in figure $AG_{1(a)}$, below

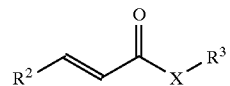

Figure AG₁₍ₐ₎

Step 1(b). amide+aldehyde→$AG_{1(b)}$.

An appropriate optically active amine and an appropriate aldehyde, below, are reacted under reducing conditions using NaBH₄ or a similar suitable boron hydride reducing agent to produce the compound represented by the structure shown in figure AG$_{1(b)}$, below, Figure AG$_{1(b)}$

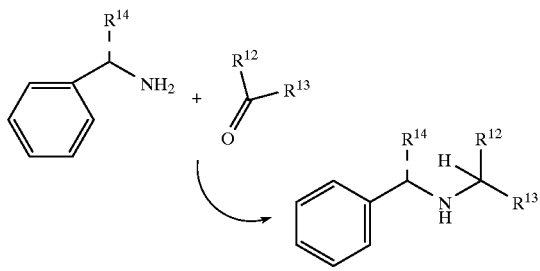

where R$^{12}$ is (C$_6$–C$_{12}$ aryl), or the aryl is substituted with one to three of the following groups, (C$_1$–C$_3$)alkyl, (C$_1$–C$_3$) alkoxy, halogen, trifluoromethyl;

R$^{13}$ is H, —(C$_1$–C$_8$)alkyl, —(C$_3$–C$_8$)cycloalkyl, —(C$_1$–C$_8$)alkyl-(C$_3$–C$_8$)cycloalkyl, —(C$_6$–C$_{12}$ aryl), —(C$_1$–C$_8$)alkyl-(C$_6$–C$_{12}$ aryl), or the aryl or alkyl is substituted with one to three of the following groups, —(C$_6$–C$_{12}$ aryl), —(C$_1$–C$_3$)alkyl, —(C$_1$–C$_3$) alkoxy, halogen, trifluoromethyl, where R$^{14}$ is —(C$_1$–C$_8$)alkyl, —(C$_3$–C$_8$)cycloalkyl, —(C$_1$–C$_8$)alkyl-(C$_3$–C$_8$)cycloalkyl, —(C$_6$–C$_{12}$ aryl), —(C$_1$–C$_8$)alkyl-(C$_6$–C$_{12}$ aryl), or the aryl or alkyl is substituted with one to three of the following groups, —(C$_6$–C$_{12}$ aryl), —(C$_1$–C$_3$)alkyl, —(C$_1$–C$_3$) alkoxy, halogen, trifluoromethyl.

Step 2. AG$_{1(a)}$+AG$_{1(b)}$→AG$_2$.

A compound represented by the structure shown in figure AG$_{1(a)}$ is reacted with a compound represented by the deprotonated form of the structure shown in figure AG$_{1(b)}$. Deprotonation is carried out with an appropriate base such as n-BuLi, to produce the compounds represented by the structures shown in figure AG$_2$, below, Figure AG$_2$

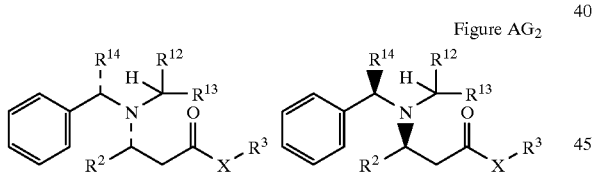

Step 3. AG$_2$→AG$_3$

Since R$^{12}$ is aryl, the nitrogen may be deprotected. The carbon nitrogen bonds are hydrogenolytically cleaved with an appropriate reducing agent such as Pearlman's catalyst, 10 percent paladium hydroxide on charcoal, to obtain the compounds represented by the structure shown in figure AG$_3$, below.

Figure AG$_3$

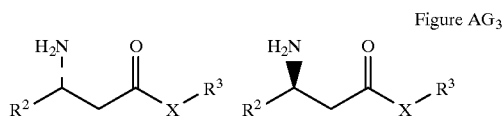

Compounds represented by the structure shown in figure AG$_3$ can then be used in the reactions of CHART B.

Examples from Chart A–Chart AX1

The specific procedures and examples described below, shown in CHART AX1 are to be construed as merely illustrative of the procedure described above, and do not impose limitations upon the general reaction schemes in any manner whatsoever. Those skilled in the art will promptly recognize appropriate variations from the procedures both as to reactants as well as to reaction conditions and techniques.

Step 1(a). Preparation of t-butyl crotonate.

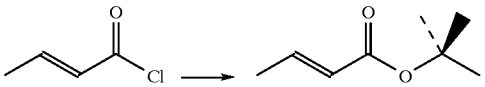

The starting materials for this step are commercially available. Shown above is Crotyl chloride and the product t-butyl crotonate.

A solution of t-BuOH (0.50 mol, 37.1 g, 47.8 mls) in THF (500 mls) is cooled to 5° C.; then over a 30 minute period n-BuLi (0.56 mol., 350 ml, 1.6 M) is added to the solution. The resulting mixture is stirred for 40 minutes at room temperature. Crotyl chloride (0.50 mol., 52.3 g, 47.9 mls) in THF (250 mls) is added to the reaction mixture at room temperature over a 15 minute period. The resulting mixture is heated under reflux for 50 minutes. The reaction mixture is cooled to 0° C. and ice-water (800 mls) is added. The layers are separated and the aqueous layer is extracted with Et$_2$O (3×600 mls). The organic phases are combined, dried over Na$_2$SO$_4$, filtered and concentrated by rotary evaporation to give a red oil. Distillation (55° C., 22 mm) yields t-butyl crotonate: $^1$H NMR (300 MHz, CDCl$_3$) δ1.46 (s, 9H), 1.83 (dd, J is 6.9, 1.7 Hz, 3H), 5.74 (dq, J is 15.5, 1.7 Hz, 1H), 6.85 (dq, J is 15.5, 6.9 Hz, 1H).

Step 1(b). Preparation of S-benzyl-α-methylbenzylamine.

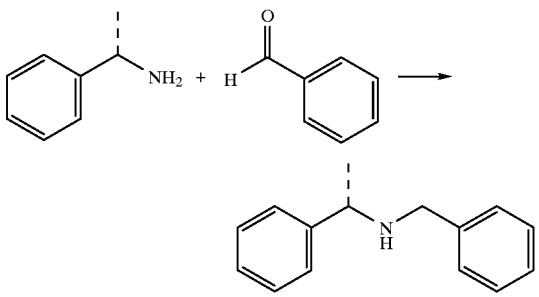

S-α-methylbenzylamine (40 g, 0.33 mol.) and benzaldehyde (35.5 g, 0.33 mol.) are combined in toluene (500 mls). The reaction mixture is refluxed until a constant amount of H$_2$O (5.2 ml) collects in a Dean-Stark trap. The reaction mixture is concentrated by rotary evaporation to yield a light yellow liquid (89.2 g) which is dissolved in ethanol (350 ml). NaBH$_4$ (12.5 g, 0.33 mol.) is added portion-wise to the reaction mixture over a one hour period. The reaction mixture is stirred at room temperature for one hour and then cooled to 0° C. 2N HCl is added dropwise over a 2-hour period to the cold reaction mixture. The reaction mixture is concentrated by rotary evaporation and the residue is partitioned between EtOAc (200 ml) and H$_2$O (100 ml). The layers are separated and the aqueous layer is back-extracted with EtOAc (2×100 mls). The organic layers are combined, dried over MgSO$_4$ and concentrated by rotary evaporation to yield a light yellow oil. Distillation (115° C., 0.75 mm Hg) yields S-benzyl-α-methylbenzylamine: $^1$H NMR (300 MHz, CDCl$_3$) δ1.37 (d, J is 6.6 Hz, 3H), 3.60 (d, J is 13.1 Hz, 1H), 3.66 (d, J is 13.1 Hz, 1H), 3.81 (q, J is 6.6 Hz, 1H), 7.23–7.36 (m, 10H).

Step 2. Preparation of t-butyl (S,S)-3-((N-benzyl)(N-methylbenzyl))aminobutyrate.

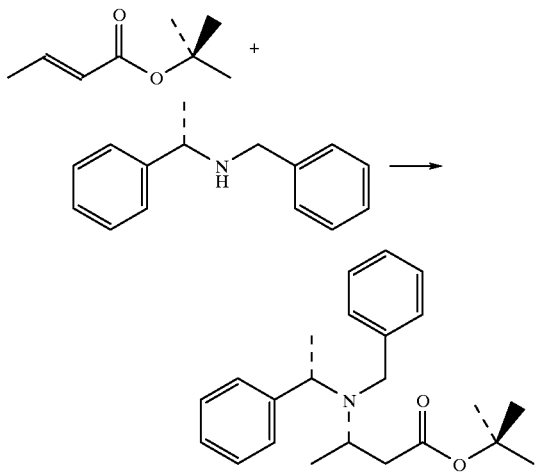

n-BuLi (158 ml, 0.25 mol.) is added via cannula to a solution of S-benzyl-α-methylbenzylamine (53.5 g, 0.25 mol.) in THF (400 mls) at 0° C. under N₂. The reaction mixture is stirred for 15 minutes and then cooled to −78° C. t-Butyl crotonate (18.0 g, 0.13 mmol) dissolved in THF (150 ml) is added via canula to the −78° C. reaction mixture over a 40-minute period. Twenty minutes after the last of the t-Butyl crotonate is added, the reaction mixture is quenched with saturated aqueous NH₄Cl (100 mls), then saturated aqueous NaCl (300 mls) is added. The layers are separated and the aqueous layer is extracted with ether (2×200 ml). The combined organic layers are washed with brine (100 mls), dried over MgSO₄, filtered and concentrated by rotary evaporation. The crude oil (72.72 g) is taken up in hexane (500 mls) and washed with 10% aqueous citric acid (buffered to pH 4, 100 ml portions) until all of the secondary amine is extracted from the organic phase. The organic phase is dried over MgSO₄, filtered and concentrated to yield t-butyl (S,S)-3-((N-benzyl)(N-methylbenzyl)) aminobutyrate: ¹H NMR (300 MHz, CDCl₃) δ1.09 (d, J is 6.7 Hz, 3H), 1.31 (d, J is 6.9 Hz, 3H), 1.37 (s, 9H), 2.00 (dd, J is 14.1, 9.1 Hz, 1H), 2.23 (dd, J is 14.1, 4.7 Hz, 1H), 3.41 (m, 1H), 3.60 (d, J is 15.0 Hz, 1H), 3.74 (d, J is 15.0 Hz, 1H), 3.87 (q, J is 7.0 Hz, 1H), 7.19–7.40 (m, 10H).

Step 3. Preparation of t-butyl (S)-3-aminobutyrate.

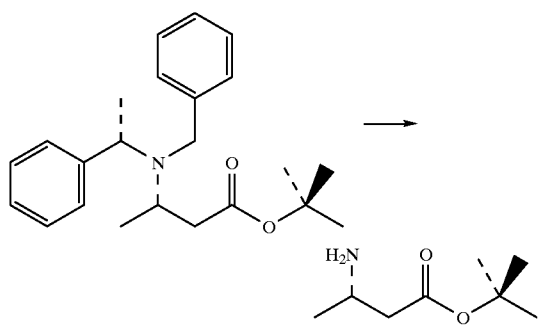

t-butyl (S,S)-3-((N-benzyl)(N-methylbenzyl)) aminobutyrate (36.5 g, 0.103 mol.) is dissolved in MeOH (500 mls). Pearlman's catalyst (5.25 g) is added and the reaction vessel is pressurized to 30 psi of H₂. After shaking for 24 hours, the reaction mixture is filtered through celite. The methanol is removed by distillation. The crude product is distilled (29 mm, 80–96° C.) to yield S-t-butyl-β-aminobutyrate: ¹H NMR (300 MHz, CDCl₃) δ1.17 (d, J is 6.5 Hz, 3H), 1.45 (s, 9H), 2.38 (dd, J is 16.0, 8.2 Hz, 1H), 2.32 (broad s, 2H), 2.29 (dd, J is 16.0, 4.7 Hz, 1H), 3.39 (m, 1H). $[\alpha]_D^{25}$ is +19.5° (c 1.65, MeOH).

CHART AX2. Using the procedures above, a more preferred starting material is to substitute ethyl crotonate for t-butyl crotonate, see step 1(a). Then, following the above procedures, prepare ethyl (S,S)-3-((N-benzyl)(N-methylbenzyl))aminobutyrate, ¹H NMR (300 MHz, CDCL₃) δ1.14 (d, J is 7, 3H), 1.16 (t, J is 7, 3H), 1.34 (d, J is 7, 3H), 2.10 (dd, J is 14, 8, 1H), 2.35 (dd, J is 14, 6, 1H), 3.43 (ddq, J is 6, 8, 7, 1H), 3.68 (d, J is 15, 1H), 3.73 (d, J is 15, 1H), 3.89 (q, J is 7, 1H), 3.92 (dq, J is 11, 7, 1H), 4.02 (dq, J is 11, 7, 1H);

in step 2 instead of t-butyl (S,S)-3-((N-benzyl)(N-methylbenzyl))aminobutyrate and finally, in step 3, prepare ethyl (S)-3-aminobutyrate instead of t-butyl (S)-3-aminobutyrate.

CHARTAX3. Using the procedures above only starting with methyl crotonate, methyl (S)-3-aminobutyrate has also been prepared. The ethyl (S)-3-aminobutyrate is slightly preferred over the methyl (S)-3-aminobutyrate. The ethyl (S)-3-aminobutyrate shown as one example in the reactions of CHARTB, the compound is shown in CHARTBX1.

The Reactions and Compounds of Chart B

CHART B shows the general reaction scheme and the major reaction Steps of the reactions involved in the synthesis of the compounds of CHART B. CHART BG shows the general reaction scheme and the 5 reaction Steps of the compounds of CHART B. CHART BX1 shows a specific reaction scheme for a single specific compound that is generally described in CHART BG. A description of the Steps and procedures from the compounds and reactions shown in CHART BG appears below. Specific examples, with detailed procedures, follow the general steps in the example section for the compounds of CHART B. Following a description of the steps are the CHARTS BG and BX1.

The Steps in Chart BG

Step 1. BG₀→BG₁. Refer to the procedures described in CHART A to obtain the starting materials for this reaction. The compound or compounds represented by the structures shown in figure BG₀₋₁, below, Figure BG₀₋₁

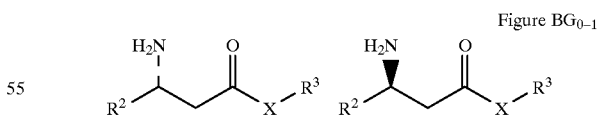

where R² and R₃ is —(C₁–C₈)alkyl, —(C₃–C₈)cycloalkyl, —(C₁–C₈)alkyl-(C₃–C₈)cycloalkyl, —(C₆–C₁₂ aryl), —(C₁–C₈)alkyl-(C₆–C₁₂ aryl), or the aryl or alkyl is substituted with one to three of the following groups, (C₆–C₁₂ aryl), (C₁–C₃)alkyl, (C₁–C₃) alkoxy, halogen, trifluoromethyl; and X is O, NH, S are reacted with a compound represented by the structure in figure BG-R₁, below, Figure BG-R₁

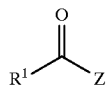

where R¹ is H, —(C₁–C₈)alkyl, —(C₃–C₈)cycloalkyl, —(C₁–C₈)alkyl-(C₃–C₈)cycloalkyl, —(C₆–C₁₂ aryl), —(C₁–C₈)alkyl-(C₆–C₁₂ aryl), —O—(C₁₋₈ alkyl), —O—(C₃₋₈ cycloalkyl), —O—(C₁₋₈ alkyl)(C₃₋₈ cycloalkyl), —O—(C₆₋₁₂ aryl), —O—(C₁₋₈ alkyl)-aryl, or the aryl or alkyl is substituted with one to three of the following groups, (C₆–C₁₂ aryl), (C₁–C₃)alkyl, (C₁–C₃) alkoxy, halogen, trifluoromethyl, and Z is Cl, N₃, S-aryl,

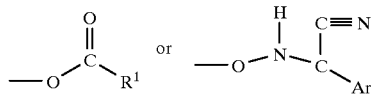

in a suitable organic solvent to yield a compound or compounds represented by the structures shown in figure BG₁₋₁, below, Figure BG₁₋₁

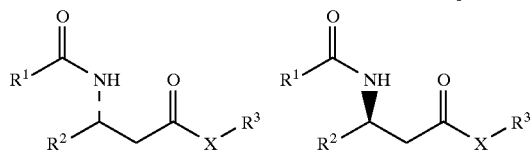

Step 2. BG₁→BG₂. To a solution of the compounds represented by the structure shown in figure BG₁ in a suitable organic solvent such as tetrahydrofuran, between a temperature of −45° C.–(−78° C.), under a nitrogen atmosphere is added a compound of the following general description, figure GRX, below.

Figure GRX

where R⁷ and R⁸ are are defined independently and are —(C₁–C₈)alkyl, —(C₃–C₈)cycloalkyl, —(C₁–C₈)alkyl-(C₆–C₁₂)aryl; and M is Li, Na, or K;

The resulting dianion is then reacted with a compound represented by the structure shown in figure GYX, below,

FIG. GYX

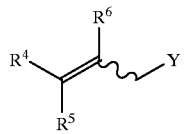

where R⁴, R⁵ and R⁶ are defined independently and are H, —(C₁–C₈)alkyl, —(C₃–C₈)cycloalkyl, —(C₁–C₈)alkyl-(C₃–C₈)cycloalkyl, —(C₆–C₁₂ aryl), —(C₁–C₈)alkyl-(C₆–C₁₂ aryl), or the aryl or alkyl is substituted with one to three of the following groups, —(C₆–C₁₂ aryl), —(C₁–C₃) alkyl, —(C₁–C₃) alkoxy, halogen, trifluoromethyl; and Y is halogen, —OTs, —OMs, —OTf to obtain a compound or compounds represented by the structures shown in figure BG₂₋₁, below.

FIG. BG₂₋₁

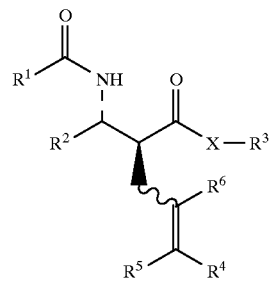

Step 3. BG₂→BG₃. BG₂ is subjected to an established method of ozonolysis, such as bubbling O₃ from an ozone generator, such as a Welsbach ozonator, through the reaction mixture, followed by treatment of the intermediate carbonyl compound with R⁹—NH₂ under reducing conditions, such as with sodium cyano borohydride, sodium triacetoxy borohydride or sodium borohydride, (in order of preference) at 0°–50° C., or a cool temperature to control heat, to obtain a compound or compounds represented by the structures shown in figure BG₃₋₁, below,

FIG. BG₃₋₁

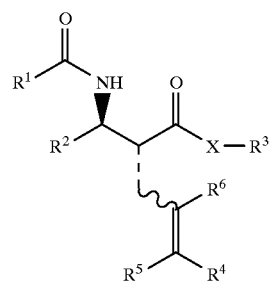

where R⁹ is H, —(C₁–C₈)alkyl, —(C₃–C₈)cycloalkyl, —(C₁–C₈)alkyl-(C₃–C₈)cycloalkyl, —(C₆–C₁₂ aryl), —(C₁–C₈)alkyl-(C₆–C₁₂ aryl), or the aryl or alkyl is substituted with one to three of the following groups, —(C₆–C₁₂ aryl), —(C₁–C₃)alkyl, —(C₁–C₃) alkoxy, halogen, trifluoromethyl.

Step 4. BG₃→BG₄. BG₃ is reduced by LAH, DIBAL, Borane, etc. to obtain the compound or compounds represented by the structures shown in figure BG$_{4\text{-}1}$, below, Figure BG$_{4\text{-}1}$

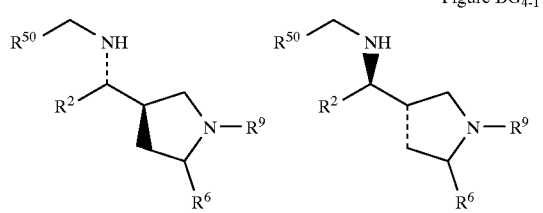

where R$^{50}$ is H, —(C$_1$–C$_8$)alkyl, —(C$_3$–C$_8$)cycloalkyl, —(C$_1$–C$_8$)alkyl-(C$_3$–C$_8$)cycloalkyl, —(C$_6$–C$_{12}$ aryl), —(C$_1$–C$_8$)alkyl-(C$_6$–C$_{12}$ aryl), or the aryl or alkyl is substituted with one to three of the following groups, (C$_6$–C$_{12}$ aryl), (C$_1$–C$_3$)alkyl, (C$_1$–C$_3$) alkoxy, halogen, trifluoromethyl. When R$^1$ is —O—(C$_{1\text{-}8}$ alkyl), —O—(C$_{3\text{-}8}$ cycloalkyl), —O—C$_{1\text{-}8}$ alkyl)(C$_{3\text{-}8}$ cycloalkyl), —O—(C$_{6\text{-}12}$ aryl), —O—(C$_{1\text{-}8}$ alkyl)-aryl, then reduction with LAH, DIBAL or Borane will always produce R$^{50}$ is H.

Step 5. BG$_4$→BG$_5$. When it is desired to make R$^9$ a protective group, where for example an alkylaryl is connected to the nitrogen atom with one carbon atom between the nitrogen and the aryl, that is where aryl is bound to the first carbon in the alkyl side chain, then this deprotection step 5 may be used. For example, if R$^9$ is benzyl, figure BG$_4$ could be hydrogenolytically cleaved with 10 percent palladium hydroxide on charcoal, H$_2$; to obtain a compound represented by the structure shown in figure BG$_5$ below.

FIG. BG$_5$

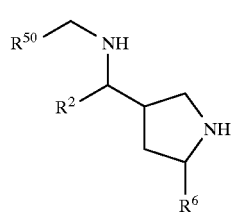

Depending upon the starting materials used, compounds represented by the structure shown by figure BG$_5$ may have one of either of the two steriochemical arrangments shown by the structures below, figure BG$_{5\text{-}1}$, FIG. BG$_{5\text{-}1}$

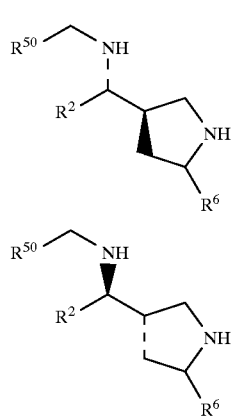

or, if the starting materials are a racemic mixture, the reaction may produce a 1:1 ratio of the combination of products shown in Figure BG$_{5\text{-}1}$, i.e. a racemic mixture.

When R$^9$ is not a protective group, as described above, step 5 cannot be performed.

Examples from Chart B

The specific procedures and examples described below, shown in CHART BX1 (t-butyl ester shown in chart, ethyl ester used below) are to be construed as merely illustrative, and do not impose limitations upon the general reaction schemes in any manner whatsoever. Those skilled in the art will promptly recognize appropriate variations from the procedures both as to reactants as well as to reaction conditions and techniques. The actual NMR data provided below each step was obtained from the racemic mixture. The specific enantiomer shown in the steps below by using the appropriate starting materials. Although the ethyl ester is shown in the steps below, the t-butyl ester could also be used as is shown in CHART BX1.

Step 1. Preparation of Ethyl (S)-3-carboxybenzylaminobutyrate.

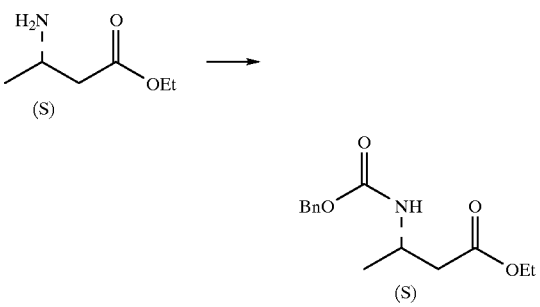

Cool a a solution of ethyl 3-aminobutyrate (20 g, 153 mmol.) in pyridine (55 ml), to 0° C. and add benzyl chloroformate (32.6 ml, 39.0 g, 229 mmol) over a 45 minute period. Stir the resulting reaction mixture at room temperature under N$_2$ for 20 hours. Partition the reaction mixture between ethyl ether and 2% (aq.) H$_2$SO$_4$. Separate the layers. The organic layer is washed with 2% (aq.) H$_2$SO$_4$, 5% (aq.) NaHCO$_3$ and brine. The organic layer was dried over MgSO$_4$, filtered and concentrated to yield ethyl 3-carboxybenzylamino butyrate: $^1$H NMR (300 MHz, CDCl$_3$) δ1.24 (d, J is 6.7 Hz, 3H), 1.25 (t, J is 7.1 Hz, 3H), 2.52 (d, J is 5.6 Hz, 2H), 4.12 (m, 1H), 4.14 (q, J is 7.1 Hz, 2H), 5.09 (s, 2H), 5.24 (broad s, 1H), 7.31–7.38 (m, 5H).

Step 2. Preparation of Ethyl (S,S)-2-(1'-(carboxybenzylamino)ethyl)-4-pentenoate.

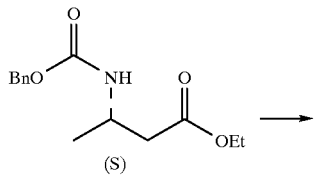

-continued

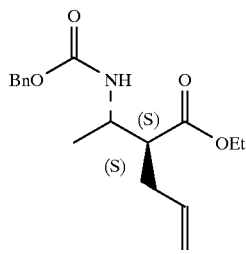

To a solution of i-Pr$_2$NH (2.93 ml, 20.88 mmol) in tetrahydrofuran (20 ml) at −30° C. and under a nitrogen atmosphere add 1.6M n-BuLi (11.5 ml, 18.37 mmol). The resulting solution of LDA was allowed to warm to −10° C. over 50 min. and was then cooled to −55° C. Ethyl (S)-3-carboxybenzylaminobutyrate (2.0 ml, 8.35 mmol), in solution in tetrahydrofuran (20 ml) at room temperature, is added during a 5 minute period to the −55° C. solution of LDA. The temperature may rise to 48° C. during this addition. The reaction is cooled to −56° C. and tetrahydrofuran (20 ml) is added over 3 minutes to the reaction mixture. After 30 minutes allylbromide (2.89 ml, 33.40 mmol) is added during a 3 minute period to the −45° C. reaction mixture. The reaction mixture is maintained at −45° C. for 20 minutes and is then allowed to warm to room temperature during a 12 hour period. The reaction mixture is combined with saturated aqueous NH$_4$Cl (100 mls) and is extracted with CH$_2$Cl$_2$ (5×100 mls). The combined organic extracts are dried over MgSO$_4$, filtered and concentrated by rotary evaporation. The resulting crude oil is chromatographed (SiO$_2$, 5:1 Hx:EtOAc) to yield ethyl (S,S)-2-[1'-(carboxybenzylamino)ethyl]-4-pentenoate: $^1$H NMR (300 MHz, CDCl$_3$) δ1.17 (d, J is 6.8 Hz, 3H), 1.25 (t, J is 7.1 Hz, 3H), 2.29 (ddd, J is 14.0, 7.0, 7.0 Hz, 1H), 2.40 (ddd, J is 14.0, 7.0, 7.0 Hz, 1H), 2.53 (m, 1H), 3.97 (m, 1H), 4.14 (q, J is 7.1 Hz, 2H), 5.03 (d, J is 10 Hz, 1H), 5.06 (d, J is 16 Hz, 1H), 5.09 (s, 2H), 5.57 (broad d, J is 9 Hz, 1H), 5.74 (ddd, J is 16, 10, 7 Hz, 1H), 7.30–7.37 (m, 5H).

Step 3. Preparation of (S,S)-1-benzyl-2-oxo-3-(1'-(carboxybenzylamino)ethyl)pyrrolidine.

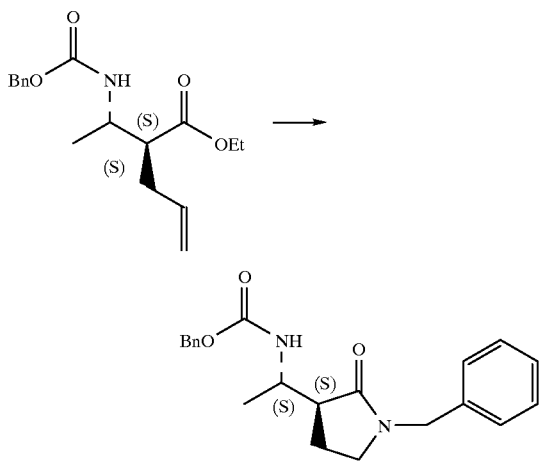

Ethyl (S,S)-2-[1'-(carboxybenzylamino)ethyl]-4-pentenoate (2.19 g, 7.18 mmol) is dissolved in MeOH (50 ml) and the resulting solution cooled to −78° C. O$_3$, from a Welsbach ozonator set at the standard settings, is bubbled through the reaction mixture until starting material can no longer be detected by thin-layer chromatography (2:1 hexane:EtOAc). Dimethyl sulfide (5 ml) is added to the reaction mixture which is allowed to warm to room temperature and is then concentrated by rotary evaporation. The crude aldehyde is dissolved in methanol (25 ml) and tetrahydrofuran (25 ml) and the resulting solution is cooled to 0° C. under a nitrogen atmosphere. Benzyl amine (4.06 ml, 37.15 mmol) followed by acetic acid (4.68 ml, 81.73 mmol) is added to the reaction mixture which is then stirred at 0° C. for 12 min. NaCNBH$_3$ (0.95 g, 14.86 mmol) is added to the reaction mixture which is allowed to warm to room temperature and continuously stirred for a 24 hour period. The reaction mixture is adjusted to pH 9 with 1N NaOH and the resulting mixture is partitioned between EtOAc and water. The layers are separated and the aqueous layer is extracted with EtOAc. The combined organic layers are dried over MgSO$_4$, filtered and then concentrated by rotary evaporation. The crude product is purified by chromatography (1:1 hexane:EtOAc) to give (S,S)-1-benzyl-2-oxo-3-[1'(carboxybenzylamino)ethyl]pyrrolidine: $^1$H NMR (300 MHz, CDCl$_3$) δ1.30 (d, J is 7 Hz, 3H), 1.77 (ddd, J is 16, 12, 9 Hz, 1H), 2.04 (m, 1H), 2.59 (ddd, J is 9, 9, 4 Hz, 1H), 3.04–3.09 (m, 2H), 3.95 (m, 1H), 4.34 (s, 2H), 5.01 (s,2H), 5.11 (broad s, 1H), 7.10–7.28 (m, 10H).

Step 4. Preparation of (R,S)-1-benzyl-3-[1'-(methylamino)ethyl]pyrrolidine.

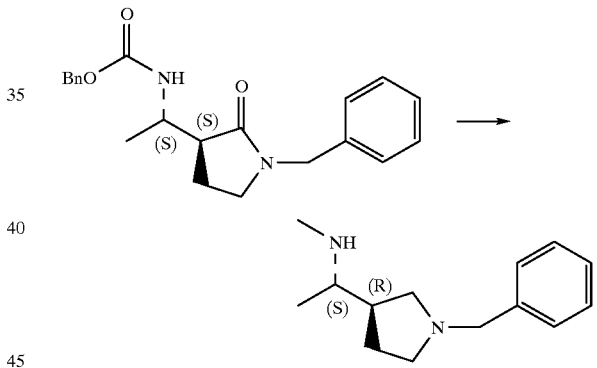

(S,S)-1-benzyl-2-oxo-3-[1'-(carboxybenzylamino)ethyl]pyrrolidine (0.51 g, 1.44 mmol) is dissolved in tetrahydrofuran (20 ml) under a N$_2$ atmosphere. LAH (0.32 g, 8.43 mmol) is added and the reaction mixture is refluxed for 12 hours. The reaction mixture is cooled to 0° C., diluted with Et$_2$O and quenched with 15% aqueous NaOH. The resulting mixture is filtered through a celite pad which is then washed carefully with Et$_2$O. The filtrate is washed with 15% aqueous NaOH and the aqueous layer extracted with Et$_2$O. The combined Et$_2$O layers are dried over MgSO$_4$, filtered and concentrated under a stream of N$_2$ to give crude (R,S)-1-benzyl-3-[1'-(methylamino)ethyl]pyrrolidine: $^1$H NMR (300 MHz, CDCl$_3$) δ1.04 (d, J is 6 Hz, 3H), 1.52 (m, 1H), 1.93 (m, 1H), 2.17 (m, 1H), 2.25 (dd, J is 16, 8 Hz, 1H), 2.37 (s, 3H), 2.33–2.49 (m, 2H), 2.56 (dd, J is 15, 8 Hz, 1H), 2.77 (dd, J is 8, 8 Hz, 1H), 3.58 (d, J is 12.8 Hz, 1H), 3.60 (d, J is 12.8 Hz, 1H), 7.23–7.36 (m, 5H). This crude material is suitable for use in Step 5.

Step 5. Preparation of (R,S)-3-[1'-(methylamino)ethyl]pyrrolidine.

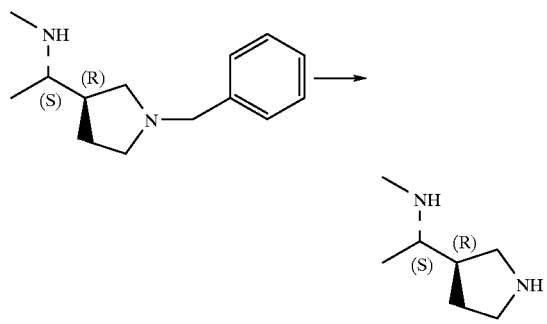

(R,S)-1-benzyl-3-[1'-(methylamino)ethyl]pyrrolidine (0.51 g of crude product) is dissolved in MeOH (10 ml) under a $N_2$ atmosphere, Pearlman's catalyst and ammonium formate (0.89 g, 14.11 mmol) are then added. The reaction mixture is refluxed for 12 hours. The reaction mixture is then diluted with $CH_2Cl_2$:MeOH (1:1) and filtered through a celite pad. The filtrate is washed with 15% aqueous NaOH:brine (1:1) and the aqueous layer is back extracted with $CH_2Cl_2$ (2×). The combined organic layers are dried over $MgSO_4$, filtered and concentrated under a stream of $N_2$ to give crude (R,S)-3-[1'-(methylamino)ethyl]pyrrolidine: $^1H$ NMR (300 MHz, $CDCl_3$) δ1.05 (d, J is 6.3 Hz, 3H), 1.43 (ddd, J is 17, 12, 9 Hz, 1H), 1.87 (m, 1H), 2.02 (dd, J is 16, 8 Hz, 1H), 2.38 (s, 3H), 2.41 (m, 1H), 2.61 (broad s, 2H), 2.65 (dd, J is 11, 8 Hz, 1H), 2.91–3.00 (m, 2H), 3.13 (dd, J is 11, 8 Hz, 1H). This material is suitable for use in various reactions including but not limited to the synthesis of quinolones.

The Reactions and Compounds of Chart C-G

The procedures below refer to CHART C-G.

Step 1(b)

Formation of $CG_{1(b)}$. An appropriate optically active amine, such as a compound represented by the structures shown in Figure CG-$R_1$, below,

FIG. CG-$R_1$

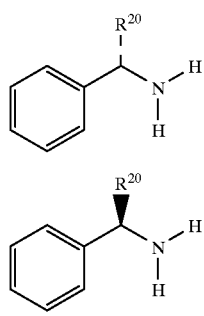

where $R^{20}$ is —($C_1$–$C_8$)alkyl, —($C_3$–$C_8$)cycloalkyl, —($C_1$–$C_8$)alkyl-($C_3$–$C_8$)cycloalkyl, —($C_6$–$C_{12}$ aryl), —($C_1$–$C_8$)alkyl-($C_6$–$C_{12}$ aryl), or the aryl or alkyl is substituted with one to three of the following groups, —($C_6$–$C_{12}$ aryl), —($C_1$–$C_3$)alkyl, —($C_1$–$C_3$) alkoxy, halogen, trifluoromethyl, is condensed with a carbonyl compound, such as one represented by the structure shown in Figure CG-$R_2$ below,

FIG. CG-$R_2$

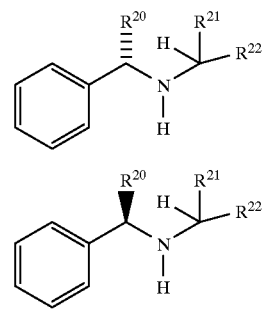

where $R^{21}$ and $R^{22}$ are defined independently and are H, —($C_1$–$C_8$)alkyl, —($C_3$–$C_8$)cycloalkyl, —$C_1$–$C_8$)alkyl-($C_3$–$C_8$)cycloalkyl, —($C_6$–$C_{12}$ aryl), —($C_1$–$C_8$)alkyl-($C_6$–$C_{12}$ aryl), or the aryl or alkyl is substituted with one to three of the following groups, —($C_6$–$C_{12}$ aryl), —($C_1$–$C_3$) alkyl, —($C_1$–$C_3$) alkoxy, halogen, trifluoromethyl; under reducing conditions using $NaBH_4$ or a similar suitable boron hydride reducing agent in a suitable solvent such as THF to obtain compounds represented by the structures shown in figure $CG_{1(b)}$ below, FIG. $CG_{1(b)}$

Step 2

$CG_{1(a)} + CG_{1(b)} \rightarrow CG_2$. A compound represented by the structures shown in $CG_{1(a)}$, below, FIG. $CG_{1(a)}$

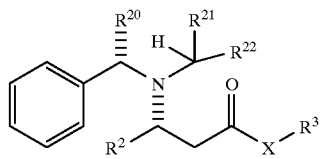

where, $R^2$ and $R^3$ are independently, lower alkyl alkylaryl, or optionally substituted aryl, and and where X is O, NH, S; undergoes a Michael Addition reaction, between 0 and –100° C. temperature, but preferably at –70 to –80° C., with a compound represented by the deprotonated form of the structures shown in figure $CG_{1(b)}$. Deprotonation is performed between 0 and –100° C., but preferably between –30 to –50° C., with an appropriate base such as n-BuLi, to produce compounds, after coupling, represented by the structures shown in figure $CG_2$ below,

FIG. $CG_2$

-continued

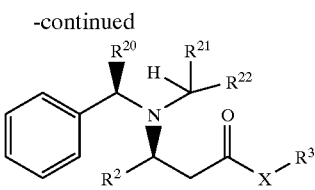

Step 3

CG$_2$→CG$_3$. Since the amine nitrogen of structures CG$_2$ has a benzyl substituent, this nitrogen may be deprotected. The carbon nitrogen bonds are hydrogenolytically cleaved with an appropriate reducing agent such as Pearlman's catalyst, 20 percent palladium hydroxide on charcoal, in an appropriate solvent, such as EtOH, to obtain the compounds represented by the structures shown in figure CG$_3$.

FIG. CG$_3$

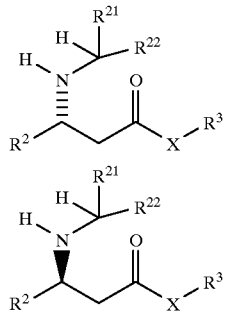

Compounds represented by the structures shown in figure CG$_3$ are then used as starting materials for the reactions of CHARTS D.

The Reactions and Compounds of Chart D-G.

The procedures below refer to CHART D-G.
Step 1
DG$_0$→DG$_1$. Refer to the procedures described in CHART C to obtain the starting materials for this reaction. The compounds represented by the structures in figure DG$_0$, below,

FIG. DG$_0$

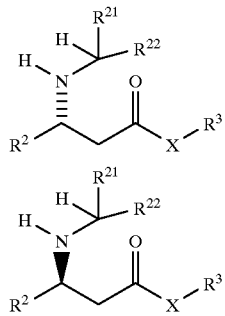

(Where $R^{21}$ and $R^{22}$ are defined independently and are H, —(C$_1$-C$_8$)alkyl, —(C$_3$-C$_8$)cycloalkyl, —(C$_1$-C$_8$)alkyl-(C$_3$-C$_8$)cycloalkyl, —(C$_6$-C$_{12}$ aryl), —(C$_1$-C$_8$)alkyl-(C$_6$-C$_{12}$ aryl), or the aryl or alkyl is substituted with one to three of the following groups, —(C$_6$-C$_{12}$ aryl), —(C$_1$-C$_3$) alkyl, —(C$_1$-C$_3$) alkoxy, halogen, trifluoromethyl. Where $R^2$ and $R^3$ are defined independently and are lower alkyl, alkylaryl, or optionally substituted aryl) and where X is O, NH, S; are dissolved in a suitable organic solvent such as tetrahydrofuran, and then added, between a temperature of −50° C. and 0° C., preferably around −30 or −40° C., in a nitrogen atmosphere, to a solution of a compound of the description in figure GRX, dissolved in a suitable organic solvent.

FIG. GRX

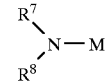

(Where $R^7$ and $R^8$ are defined independently and are —(C$_1$-C$_8$)alkyl, —(C$_3$-C$_8$)cycloalkyl, —(C$_1$-C$_8$)alkyl-(C$_6$-C$_{12}$)aryl; where M is Li, Na, or K) Note that the compounds represented by the figure GRX contain R groups, $R^7$ and $R^8$, that are not incorporated into the desired compounds, figure GRX represents a compound that only acts as a base. This use of the compounds of Figure GRX applies to all the reactions of this invention. The resulting anion or dianion is then reacted with a compound represented by the structure shown in figure GYX, below,

FIG. GYX

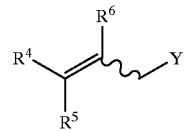

(Where $R^4$, $R^5$, and $R^6$ are independent and are H, alkyl, alkylaryl, or optionally substituted aryl, and where Y is halogen, —OTs, —OMs, or —OTf.) to obtain a compound represented by the structures shown in figure DG$_1$, below.

FIG. DG$_1$

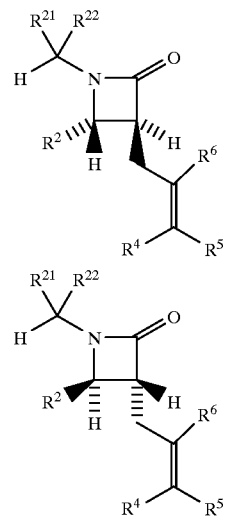

Step 2
DG$_1$→DG$_2$. DG$_1$ is subjected to an established method of ozonolysis, such as bubbling O$_3$ from an ozone generator, such as a Welsbach ozonator, through the reaction mixture in an appropriate solvent, such as water or methanol, followed by reduction of the intermediate ozonide with an appropriate boron hydride reducing agent such as NaBH$_4$ or LiBH$_4$ to obtain a compound represented by the structures shown in figure DG$_2$, below.

FIG. DG₂

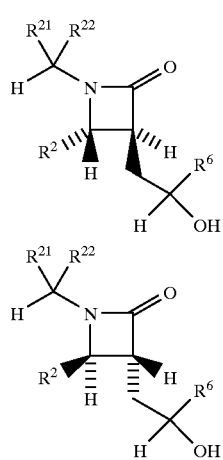

Step 3

DG₂→DG₃. DG₂ is treated with an appropriate amine base, such as triethylamine, and an activating agent, such as methanesulfonyl chloride in a solvent such as tetrahydrofuran or toluene to obtain a compound represented by the structures shown in figure DG₃, where Ms is mesylate, below.

FIG. DG₃

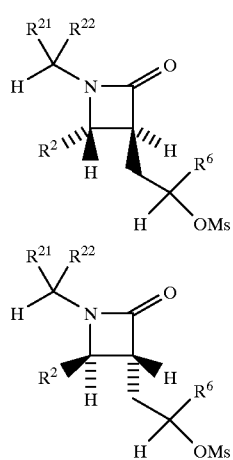

Step 4

DG₃→DG4. DG₃ is treated in an appropriate solvent such as toluene or THF with an amine represented by the structure shown in figure DG-R₁ below,

FIG. DG-R₁

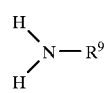

(where R⁹ is defined previously) to obtain a compound represented by the structures shown in figure DG₄ below.

FIG. DG₄

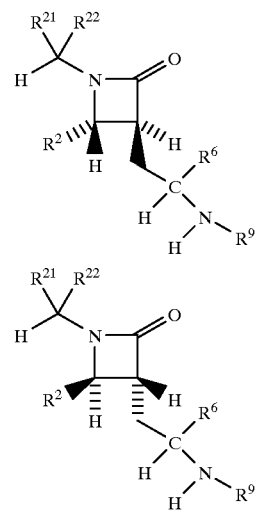

Step 5

DG₄→DG₅. In the same reaction vessel as step 4, above, DG₄ thermally isomerizes to give a compound represented by the structures shown in figure DG₅ below.

FIG. DG₅

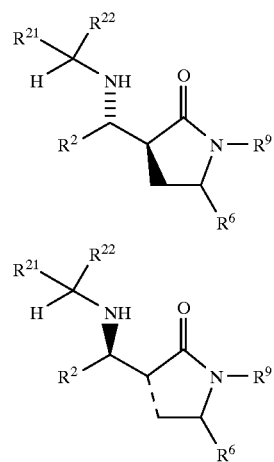

Step 6

DG₅→DG₆. DG₅ is treated with a suitable reducing agent such as LiAlH₄, DIBAL or Borane in a suitable solvent such as THF to obtain a compound or compounds represented by the structures shown in figure DG₆, below.

FIG. DG₆

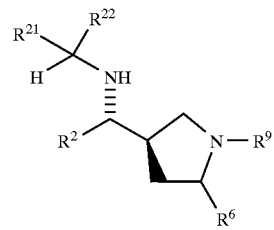

-continued

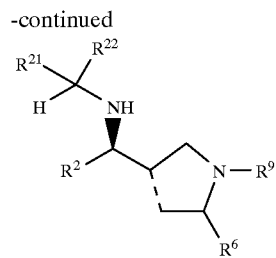

Step 7

DG$_6$→DG$_7$. When R$^9$ is a C$_1$–C$_6$ alkyl the reaction stops, and if R$_9$ is an alkylaryl that is connected to the nitrogen atom with more than one carbon atom between the nitrogen and aryl, the reaction will also stop. When it is desired to make R$^9$ a protective group, where for example an alkylaryl is connected to the nitrogen atom with one carbon atom between the nitrogen and the aryl, that is where the aryl is bound to the first carbon atom in the alkyl side chain, then this deprotection step 7 may be used. For example if R$^9$ is benzyl, figure DG$_6$ could be hydrogenolytically cleaved with 20 percent palladium hydroxide on charcoal; to obtain a compound represented by the structures shown in figure DG$_7$ below,

FIG. DG$_7$

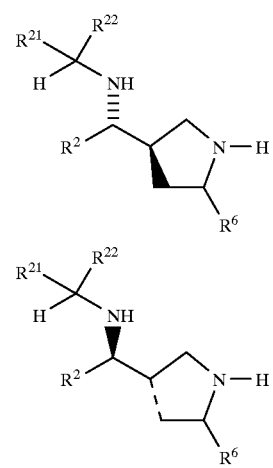

Depending upon the starting materials used, compounds represented by the structures on the left side of the figures or the right side of the figures or, if the starting materials are a racemic mixture, the reaction may produce a 1:1 ratio of compounds represented on both sides of the figure DG$_7$, i.e. a racemic mixture.

Examples of Compounds from Chart D-G

Using appropriate starting materials using the procedures shown in CHART D, can be used to make the following compounds:

3-(1'-(S)-benzylamino)ethyl)pyrrolidine and 3-(1'-(S)-methylamino)ethyl)pyrroidine.

3-(1'-(S)-benzylamino)ethyl)pyrrolidine and 3-(1'-(S)-ethylaminoethyl)pyrrolidine.

The Reactions and Compounds of Chart E-G

The procedures below, which are the more preferred procedures, refer to CHART E-G.

Step 1(a)

Formation of EG$_{1(b')}$. A compound represented by the structures shown in Figure EG-R$_1$, below,

FIG. EG-R$_1$

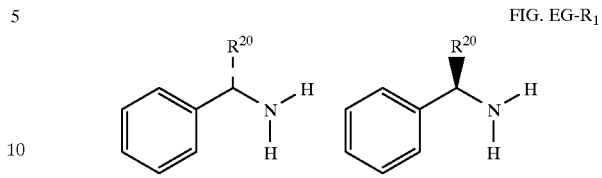

(where R$^{20}$ is —(C$_1$–C$_8$)alkyl, —(C$_3$–C$_8$)cycloalkyl, —(C$_1$–C$_8$)alkyl-C$_3$–C$_8$)cycloalkyl, —(C$_6$–C$_{12}$ aryl), —(C$_1$–C$_8$)alkyl-(C$_6$–C$_{12}$ aryl), or the aryl or alkyl is substituted with one to three of the following groups, —(C$_6$–C$_{12}$ aryl), —(C$_1$–C$_3$)alkyl, —(C$_1$–C$_3$) alkoxy, halogen, trifluoromethyl,), is condensed with a compound represented by the structure shown in figure EG-R$_2$ below,

FIG. EG-R$_2$ $$R^{24}\overset{O}{\underset{}{\|}}O^{R^{23}}$$

(where R$^{23}$ is —(C$_1$–C$_8$)alkyl, —(C$_3$–C$_8$)cycloalkyl, —(C$_1$–C$_8$)alkyl-(C$_3$–C$_8$)cycloalkyl, —(C$_6$–C$_{12}$ aryl), —(C$_1$–C$_8$)alkyl-(C$_6$–C$_{12}$ aryl), or the aryl or alkyl is substituted with one to three of the following groups, —(C$_6$–C$_{12}$ aryl), —(C$_1$–C$_3$)alkyl, —(C$_1$–C$_3$) alkoxy, halogen, trifluoromethyl;

where R$^{24}$ is H, —(C$_1$–C$_8$)alkyl, —(C$_3$–C$_8$)cycloalkyl, —(C$_1$–C$_8$)alkyl-(C$_3$–C$_8$)cycloalkyl, —(C$_6$–C$_{12}$ aryl), —(C$_1$–C$_8$)alkyl-(C$_6$–C$_{12}$ aryl), or the aryl or alkyl is substituted with one to three of the following groups, —(C$_6$–C$_{12}$ aryl), —(C$_1$–C$_3$)alkyl, —(C$_1$–C$_3$) alkoxy, halogen, trifluoromethyl;

to obtain a compound represented by the structures shown in Figure EG$_{1(b')}$ below, FIG. EG$_{1(b')}$

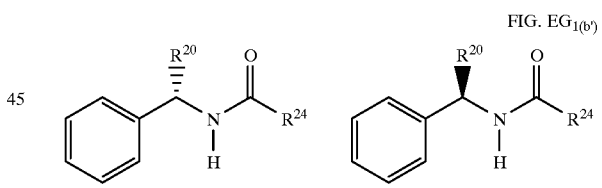

Step 1(b)

EG$_{1(b')}$→EG$_{1(b)}$. EG1$_{(b')}$ is treated with an appropriate reducing agent such as LiAlH$_4$, DIBAL or Borane in a suitable solvent such as THF to obtain compounds represented by the structures shown in figure EG$_{1(b)}$, below.

FIG. EG$_{1(b)}$

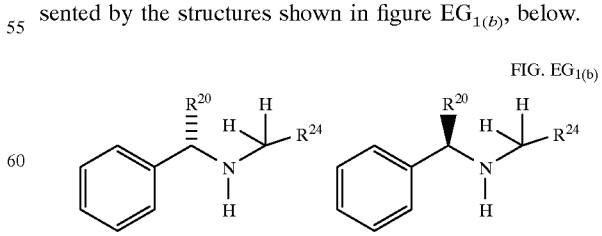

Step 2

EG$_{1(a)}$+EG$_{1(b)}$→EG$_2$ A compound represented by the structures shown in EG$_{1(a)}$, below,

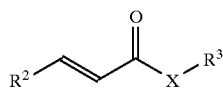

FIG. EG$_{1(a)}$ (where R$^2$ are R$^3$ are independently, lower alkyl, arlkylaryl, or optionally substituted aryl), where X is O, NH, S; undergoes a Michael Addition reaction with a compound represented by the deprotonated form of the structures shown in figure EG$_{1(b)}$. Deprotonation is carried out with an appropriate base such as n-BuLi, to produce compounds, after coupling, represented by the structures shown in figure EG$_2$, below.

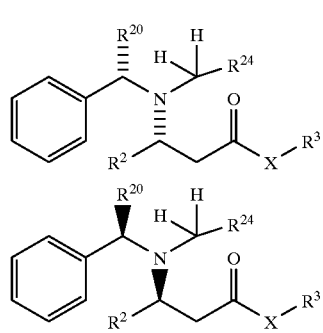

FIG. EG$_2$

Step 3

EG$_2 \rightarrow$ EG$_3$. Since the amine nitrogen of structures EG$_2$ has a benzyl substituent, this nitrogen may be deprotected. The carbon nitrogen bonds are hydrogenolytically cleaved with an appropriate reducing agent such as Pearlman's catalyst, 20 percent palladium hydroxide on charcoal, in an appropriate solvent, such as EtOH, to obtain the compounds represented by the structures shown in figure EG$_3$.

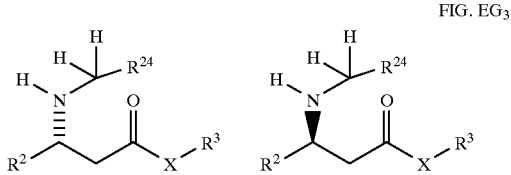

FIG. EG$_3$

The compounds represented by the structures shown in figure EG$_3$ are used as the starting materials for the reactions of CHARTS F, F-G & F-X.

The Reactions and Compounds of Chart F-G

The procedures below refer to CHART FG.

Step 1

FG$_0 \rightarrow$ FG$_1$. Refer to the procedures described in CHART E to obtain the starting materials for this reaction. The compounds represented by the structures shown in figure FG$_0$, below,

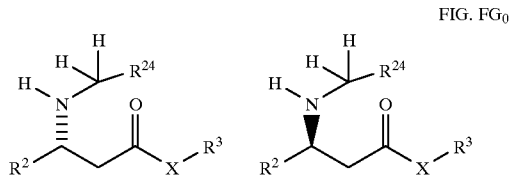

FIG. FG$_0$ (Where R$^{24}$ is H, —(C$_1$–C$_8$)alkyl, —(C$_3$–C$_8$)cycloalkyl, —(C$_1$–C$_8$)alkyl-(C$_3$–C$_8$)cycloalkyl, —(C$_6$–C$_{12}$ aryl), —(C$_1$–C$_8$)alkyl-(C$_6$–C$_{12}$ aryl), or the aryl or alkyl is substituted with one to three of the following groups, —(C$_6$–C$_{12}$ aryl), —(C$_1$–C$_3$)alkyl, —(C$_1$–C$_3$)alkoxy, halogen, trifluoromethyl; and where X is O, NH, or S; and where R$^2$ and R$^3$ are defined independently and are lower alkyl, alkylaryl, or optionally substituted aryl) are dissolved in a suitable organic solvent such as tetrahydrofuran, and added, between a temperature of –50° C. and 0° C., in an inert atmosphere or an atmosphere without water, preferably about –30 or –40° C., in a nitrogen atmosphere; to a solution of a compound represented by the structures shown in figure FG-R$_1$, below.

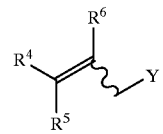

FIG. FG-R$_1$ (Where R$^9$ is H, —(C$_1$–C$_8$)alkyl, —(C$_3$–C$_8$)cycloalkyl, —(C$_1$–C$_8$)alkyl-(C$_3$–C$_8$)cycloalkyl, —(C$_6$–C$_{12}$ aryl), —(C$_1$–C$_8$)alkyl-(C$_6$–C$_{12}$ aryl), or the aryl or alkyl is substituted with one to three of the following groups, —(C$_6$–C$_{12}$ aryl), —(C$_1$–C$_3$)alkyl, —(C$_1$–C$_3$) alkoxy, halogen, trifluoromethyl). The resulting anion or dianion is then reacted with a compound represented by the structures shown in figure GYX, below,

FIG. GYX (Where R$^4$, R$^5$, and R$^6$ are independent and are H, alkyl, alkylaryl, or optionally substituted aryl, and where Y is halogen, —OTs, —OMs, or —OTf) to obtain a compound represented by the structures shown in figure FG$_1$, below,

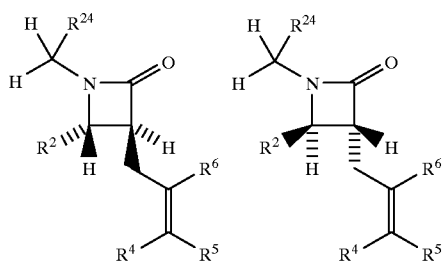

FIG. FG$_1$

Step 2

FG$_1 \rightarrow$ FG$_2$. FG$_1$ is subjected to an established method of ozonolysis, such as bubbling O$_3$ from an ozone generator, such as a Welsbach ozonator, through the reaction mixture in an appropriate solvent such as water or methanol, followed by treatment of the intermediate ozonide with an appropriate boron hydride reducing agent such as $NaBH_4$ or $LiBH_4$ to obtain a compound represented by the structures shown in figure $FG_2$, below.

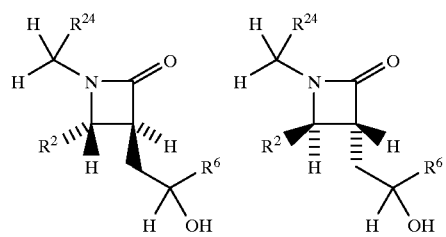

FIG. $FG_2$

Step 3

$FG_2 \rightarrow FG_3$. $FG_2$ is treated with an appropriate amine base, such as triethylamine, and methanesulfonyl chloride in a solvent such as tetrahydrofuran or toluene to obtain a compound represented by the structures shown in figure $FG_3$, where Ms is mesylate, below.

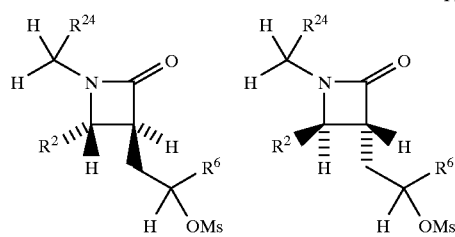

FIG. $FG_3$

Step 4

$FG_3 \rightarrow FG_4$. $FG_3$ is treated in an appropriate solvent such as toluene or THF with an amine represented by the structure shown in figure $FG-R_1$ below,

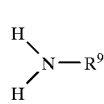

Figure $FG-R_1$ (where $R^9$ is defined earlier) to obtain a compound represented by the structures shown in figure $FG_4$ below,

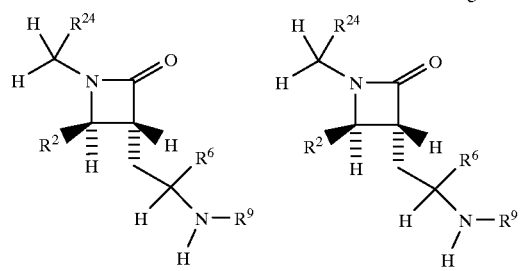

Figure $FG_4$

Step 5

$FG_4 \rightarrow FG_5$. In the same reaction vessel as step 4 above, $FG_4$ thermally isomerizes to give a compound represented by the structures shown in figure $FG_5$ below,

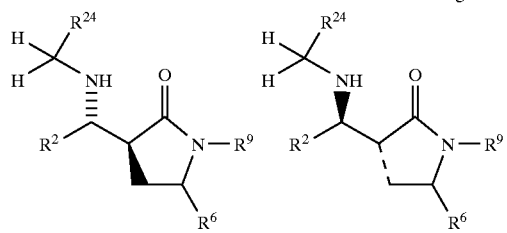

Figure $FG_5$

Step 6

$FG_5 \rightarrow FG_6$. $FG_5$ is treated with a suitable reducing agent such as $LiAlH_4$, DIBAL or Borane in a suitable solvent such as THF to obtain a compound represented by the structures shown in figure $FG_6$ below,

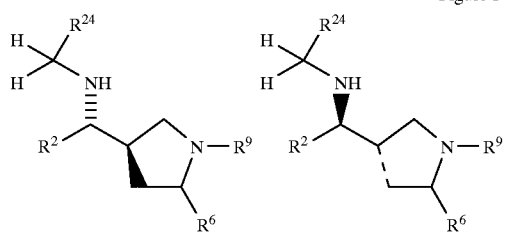

Figure $FG_6$

Step 7

$FG_6 \rightarrow FG_7$. When $R^9$ is a $C_1-C_6$ alkyl the reaction stops, and if $R_9$ is an alkylaryl that is connected to the nitrogen atom with more than one carbon atom between the nitrogen and aryl, the reaction will also stop. When it is desired to make $R^9$ a protective group, where for example an alkylaryl is connected to the nitrogen atom with one carbon atom between the nitrogen and the aryl, that is where the aryl is bound to the first carbon in the alkyl side chain, then this deprotection step 7 may be used. For example if $R^9$ is benzyl, figure $FG_6$ could be hydrogenolytically cleaved with 20 percent palladium hydroxide on charcoal; to obtain a compound represented by the structures shown in figure $FG_7$ below,

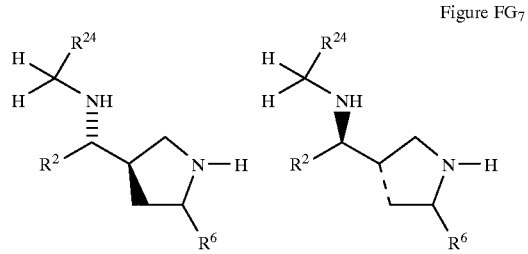

Figure $FG_7$

Depending upon the starting materials used, compounds represented by the structures on the left side of the figures or the right side of the figures or, if the starting materials are a racemic mixture, the reaction may produce a 1:1 ratio of compounds represented on both sides of the figure $FG_7$, i.e. a racemic mixture.

Examples of Compounds from Chart E–CHART EX1

The specific prodecures and examples described below, shown in CHART EX1 are to be construed as merely illustrative of the procedures described above, and do not impose limitation upon the general reaction schemes in any manner whatsoever. Those skilled in the art will promptly recognize appropriate variations from the procedures both as to reactants as well as to reaction conditions and techniques.

Step 1(a) of CHART EX1

Synthesis of N-Formyl-N-(S)-1-phenylethylamine, $EX1_{1(b')}$. Add (S)-(-)-phenylethylamine (940 g) and ethyl formate (1.83 kg) to a 5000 ml. flask. Heat the solution to reflux and stir overnight. Remove the excess ethyl formate in vacuo leaving 1.15 kg of N-formyl-(S)-1-phenylethylamine. $^{13}$CNMR (CDCl$_3$, ppm δ) 21.80, 47.61, 126.11, 127.42, 128.66, 142.73, 160.60.

STEP 1(b) of CHART EX1

Synthesis of N-Methyl-N-(S)-1-phenylethylamine, $EX_{1(b')}$. Add powdered LiAlH$_4$ (50 g) and THF (500 mL) to a 3000 ml flask. Then add a solution of N-formyl-N-(S)-1-phenylethylamine ($EX1_{1(b')}$, 100 g) in THF (500 mL) dropwise into the LiAlH$_4$ solution. Heat the solution to reflux and stir 5 hours. After reflux, cool the solution to 5° C. and slowly quench the reaction with 10% NaOH (500 mL), then extract the product with MTBE (1×2 L). Remove the solvent in vacuo, and purify the product by distillation to yield 70 g (78%) of N-methyl-N-(S)-1-phenylethylamine. $^{13}$CNMR (CDCl$_3$, ppm δ) 24.15, 34.76, 60.49, 126.84, 127.14, 128.65, 145.64.

Step 2 of CHART EX1

Synthesis of 3-(N-Methyl-N-(S)-1'-phenylethylamino) butyric acid, 2-methylpropyl ester, EX1$_2$. Add N-methyl-N-(S)-1-phenylethylamine ($EX1_{1b}$, 390.0 g, 2.88 mol, 1.1 eq) and THF (14 L) to a 22 L flask. Cool this solution to -5° C. and add n-buLi (1.80 L, 2.88 mol,) over a period of 30 min. maintaining the internal reaction temperature below 0° C. The solution is stirred at 0° C. for 30 min. and then cooled to -78° C. A pre-cooled, to -40° C., solution of isobutyl crotonate (372 g) in THF (3.0 L) is added at a rate such that the internal reaction temperature does not exceed -70° C. After the addition is complete, the reaction is stirred at -75° C. for 30 min. The reaction is quenched with saturated NH$_4$Cl until the pH is between about 9 to 11. The organic phase is separated and the solvent is removed in vacuo. The product is redissolved in EtOAc (1.5 L) and the resulting solution is filtered. The EtOAc is distilled off and MeOH (1.0 L) and 37% HCl (210 mL) are added. MTBE (5 L) is added to crystallize the amine hydrochloride salt of the 2-methylpropyl ester of 3-(N-methyl-N-(S)-1'-phenylethylamino)butyric acid. The crystalline amine hydrochloride salt is dissolved in CH$_2$Cl$_2$ (2.5 L) and water (1.0 L) is added. A 10% NaOH solution is used to adust the pH to between about 9 to 11. The organic layer is separated and the solvent is removed in vacuo to yield 290 g (65%) of 3-(N-methyl-N-(S)-1'-phenylethylamino)butyric acid, 2-methylpropyl ester. $^{13}$CNMR (CDCl$_3$, ppm δ) 14.70, 19.39, 21.97, 27.95, 32.31, 39.25, 51.43, 62.36, 70.70, 126.91, 127.40, 128.47, 146.45, 173.06.

Step 3 of CHART EX1

Synthesis of 3-(N-Methylamino)butyric acid, 2-methylpropyl ester, EX1$_3$. Add 20 wt % Pd(OH)$_2$ on carbon (5.0 g) to a 4 L Parr shaker, followed by ethanol and 3-(N-methyl-N-(S)-1'-phenylethylamino)butyric acid, 2-methylpropyl ester (EX1$_2$). Pressurize the Parr shaker to 70 atm with H$_2$. No further H$_2$ uptake after 1.5 hours indicates the reaction is complete. When the reaction is complete, filter off the catalyst and remove the solvent in vacuo to yield 65 g (100%) of 3-(N-methylamino)butyric acid, 2-methylpropyl ester. $^{13}$CNMR (CDCl$_3$, ppm δ) 16.56, 19.05, 27.60, 30.32, 37.47, 52.23, 71.42, 169.81.

Examples of Compounds from Chart F–Chart FX1

The specific prodecures and examples described below, shown in CHART FX1 are to be construed as merely illustrative of the procedures described above, and do not impose limitation upon the general reaction schemes in any manner whatsoever. Those skilled in the art will promptly recognize appropriate variations from the procedures both as to reactants as well as to reaction conditions and techniques.

Step 1 of CHART Fx1

Synthesis of 3-[(S)-2'-propenyl]-2-(S)-methyl-N-methylazetidinone, FX1$_1$. Add diisopropylamine (83.4 g) and THF (1.5 L) to a 5 ml flask. This solution is cooled to -10° C., and 1.6 M n-BuLi (515 mL, 825 mmol) is added at a rate such that the internal temperature does not exceed 0° C. After 30 min, cool the solution to -40° C., and add the 2-methylpropyl ester of 3-(N-methylamino)butyric acid (EX1$_3$, 65 g). After 30 minutes stirring add the allyl bromide (91 g) and stir an additional 30 minutes, then quench with saturated NH$_4$Cl (350 mL). The organic layer is separated, and the solvent is removed in vacuo. Purification by silica gel chromatography (33% EtOAc:heptane) yields 42 g (80%) of 3-[(S)-2'-propenyl]-2-(S)-methyl-N-methylazetidinone. $^{13}$CNMR (CDCl$_3$, ppm δ) 17.15, 25.80, 32.16, 54.46, 56.44, 116.57, 134.60, 169.12.

Step 2 of CHART FX1

Synthesis of 3-[(S)-2'-hydroxyethyl]-2-(S)-methyl-N-methylazetidinone, FX$_2$. Add 3-[(S)-2'-propenyl]-2-(S)-methyl-N-methylazetidinone (FX$_1$, 231 g) and H$_2$O (3.0 L) to a 5 L flask. Cool the solution to 0° C. then pass ozone through the solution for 8 hours. Slowly quench the ozonide intermediate with NaBH$_4$ (50 g) while maintaining the internal temperature <10° C. Bring the aqueous layer to near saturation with 1 kg NaCl, and then extract the product with CH$_2$Cl$_2$ (4×2 L). After solvent removal, the material is purified by silica gel chromatography (8% MeOH:EtOAc) to yield 160 g (69%) of 3-[(S)-2'-hydroxyethyl]-2-(S)-methyl-N-methylazetidinone. $^{13}$CNMR (CDCl$_3$, ppm δ) 17.38, 26.44, 31.63, 55.56, 56.02, 61.32, 170.61.

Step 3 of CHART FX1

Synthesis of 3-[(S)-2'-methanesulfonylethyl]-2-(S) methyl-N-methylazetidinone, FX1$_3$. Add 3-[(S)-2'-hydroxyethyl]-2-(S)methyl-N-methylazetidinone (FX1$_2$, 100 g), THF (1.0 L), and triethylamine (920 g) to a 2 L flask. The solution is cooled to -40° C. and methanesulfonyl chloride (84.0 g) is added over 20 min maintaining the internal reaction temperature about or less than -25° C. After the white precipitate of triethylaminehydrochloride is filtered off, the solution of 3-[(S)-2'-methanesulfonylethyl]-2-(S)-methyl-N-methylazetidinone in THF is used directly in the next step, but it can be isolated as a yellow oil. $^{13}$CNMR (CDCl$_3$, ppm δ) 17.39, 26.41, 28.37, 37.48, 54.21, 55.77, 68.44, 168.89.

Steps 4 and 5 of CHART FX1

Synthesis of 3-[(S)-2'-N-benzylaminoethyl]-2-(S)-methyl-N-methylazetidinone, FX1$_4$, and 3-[1'-[(S)-methylamino]ethyl]-N-benzylpyrrolidinone, FX1$_5$. A solution of benzylamine (223 g) in THF (1.0 L) is heated to reflux. A solution of 3-[(S)-2'-methanesulfonylethyl]-2-(S)-methyl-N-methylazetidinone (FX1$_3$, 1.4 kg) is dripped into the refluxing benzylamine solution from an addition funnel over 10 min. Reflux in THF is continued for 16 h until the 3-[(S)-2'-methanesulfonylethyl]-2-(S)-methyl-N-methylazetidinone, which is initially converted to 3-[(S)-2'-N-benzylaminoethyl]-2-(S)-methyl-N-methylazetidinone, is exhausted. The 3-[(S)-2'-N-benzylaminoethyl]-2-(S)-methyl-N-methylazetidinone thermally rearranges to 3-[1'-[(S)-methylamino]ethyl]-N-benzylpyrrolidinone under the reaction conditions. Removal of the THF by distillation, replacement with toluene (2.0 L), and continued reflux completes the transformation of 3-[(S)-2'-N-benzylaminoethyl]-2-(S)-methyl-N-methylazetidinone to 3-[1'-[(S)-methylamino]ethyl]-N-benzylpyrrolidinone. After solvent removal, purification by silica gel chromatography (15% MeOH:EtOAc w/1% NH$_4$OH) yielded 113 g (69%) of 3-[1'-[(S)-methylamino]ethyl]-N-benzylpyrrolidinone. $^{13}$CNMR (CDCl$_3$, ppm δ) 16.21, 20.71, 33.52, 44.68, 45.31, 46.45, 56.29, 127.41, 127.94, 128.52, 136.25, 175.51. Note that 3-[(S)-2'-N-benzylaminoethyl]-2-(S)-methyl-N-methylazetidinone, FX1$_4$, was made and isolated by an alternate route. $^{13}$CNMR (CDCl$_3$, ppm δ) 17.56, 26.25, 28.95, 47.50, 54.06, 55.66, 56.32, 127.15, 128.32, 128.60, 140.37, 170.07.

Step 6 of CHART FX1

Synthesis of 3-[1'-[(S)-methylamino]ethyl]-N-benzylpyrrolidine, FX1$_6$. Add a 1.1M solution of LiAlH$_4$ (392 mL, 431 mmol) to a 2 L flask. Heat the solution to reflux and add a solution of 3-[1'-[(S)-methylamino]ethyl]-N-benzylpyrrolidinone (FX1$_5$, 100 g) in THF (100 mL) is over 10 min. After stirring for 30 min, cool the solution to −30° C. and quench slowly with 10% NaOH (183 g). A 50% citric acid solution is added until a pH of 9 is obtained. The product is extracted with EtOAc (2×1 L), and the solvent is removed in vacuo to give 70 g (75%) of 3-[1'-[(S)-methylamino]ethyl]-N-benzylpyrrolidine. $^{13}$CNMR (CDCl$_3$, ppm δ) 17.81, 27.94, 34.09, 44.04, 54.40, 58.04, 59.28, 61.01, 127.09, 128.43, 129.04, 139.45.

Step 7 of CHART FX

Synthesis of 3-[1'-[(S)-methylamino]ethyl]benzylpyrrolidine, FX1$_7$. Add 20 wt % Pd(OH)$_2$ on carbon (12.0 g) to a 3 L autoclave followed by methanol and 3-[1'-[(S)-methylamino]ethyl]-N-benzylpyrrolidine (FX$_6$, 112 g) The autoclave is pressurized to 70 atm with H$_2$ and heated to 65° C. No H$_2$ uptake after 18 hours indicates the reaction is complete. The catalyst is filtered off, and the solvent is removed in vacuo to yield 70 g (100%) of 3-[1'-[(S)-methylamino]ethyl]benzylpyrrolidine. $^{13}$CNMR (CDCl$_3$, ppm δ) 17.85, 29.37, 33.70, 45.89, 46.76, 50.34, 58.44.

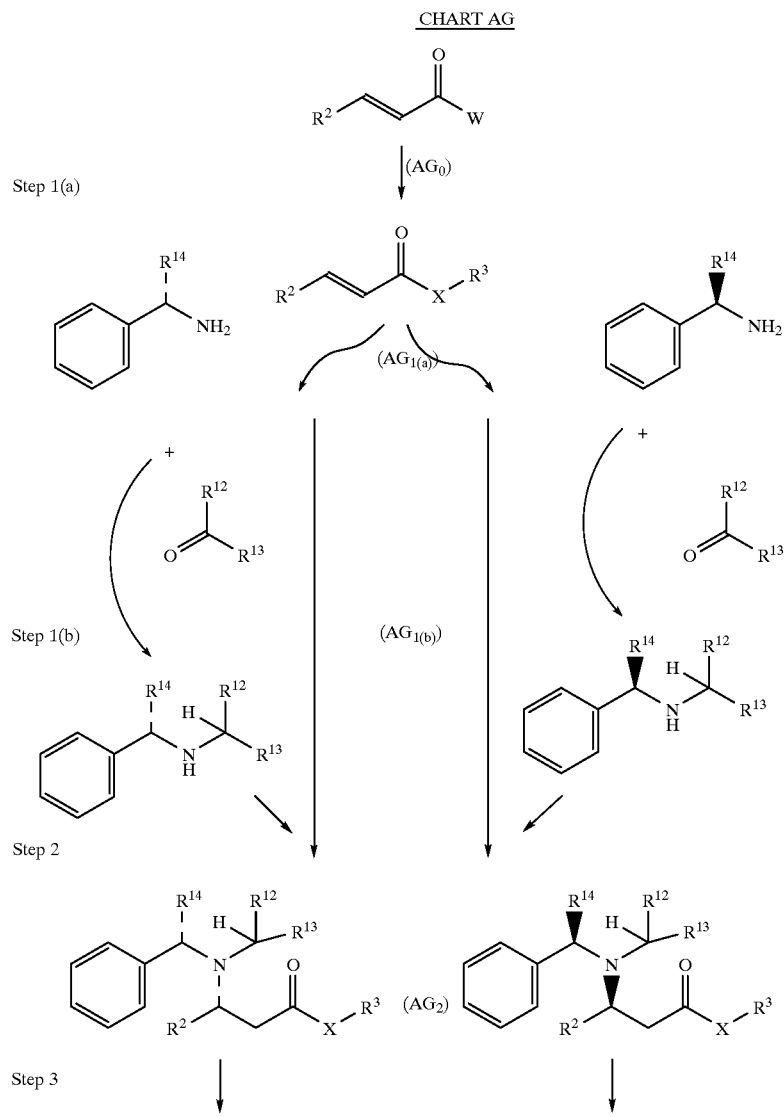

-continued
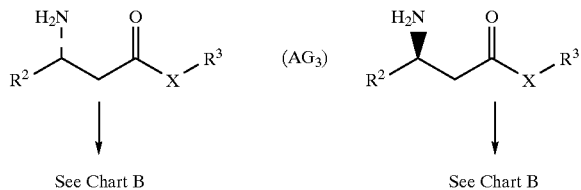
CHART AX1
Step 1(a)
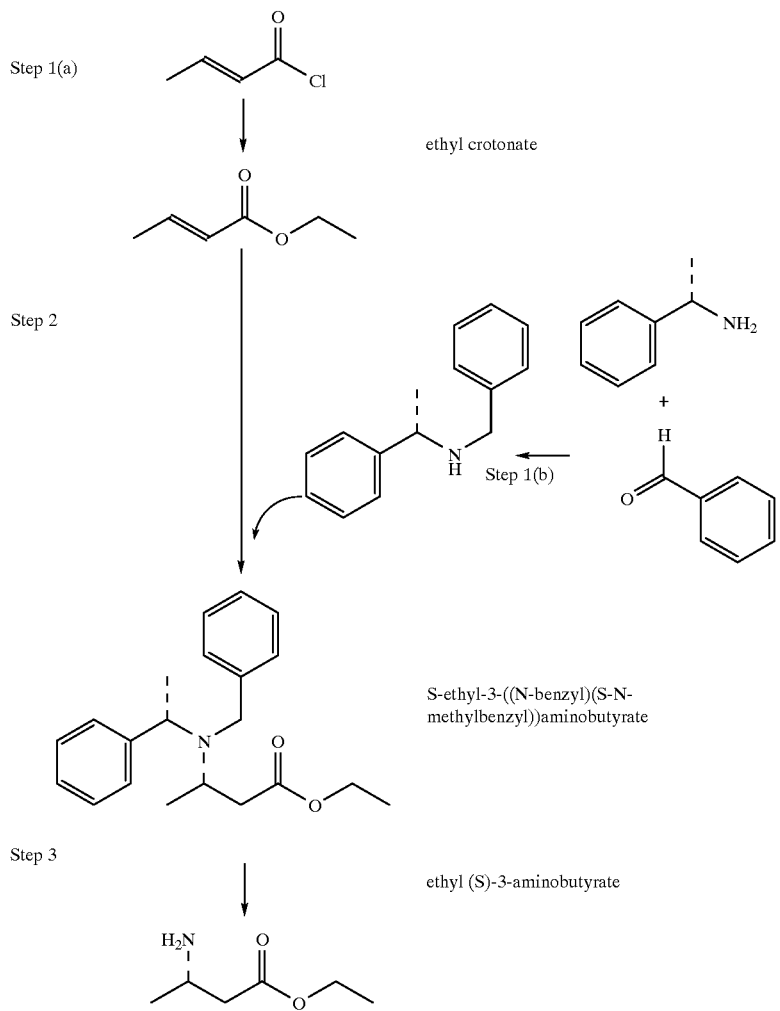
ethyl crotonate
Step 2
S-ethyl-3-((N-benzyl)(S-N-methylbenzyl))aminobutyrate
Step 3
ethyl (S)-3-aminobutyrate
CHART BG
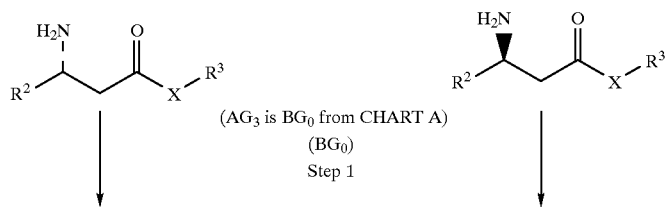
(AG₃ is BG₀ from CHART A)
(BG₀)
Step 1

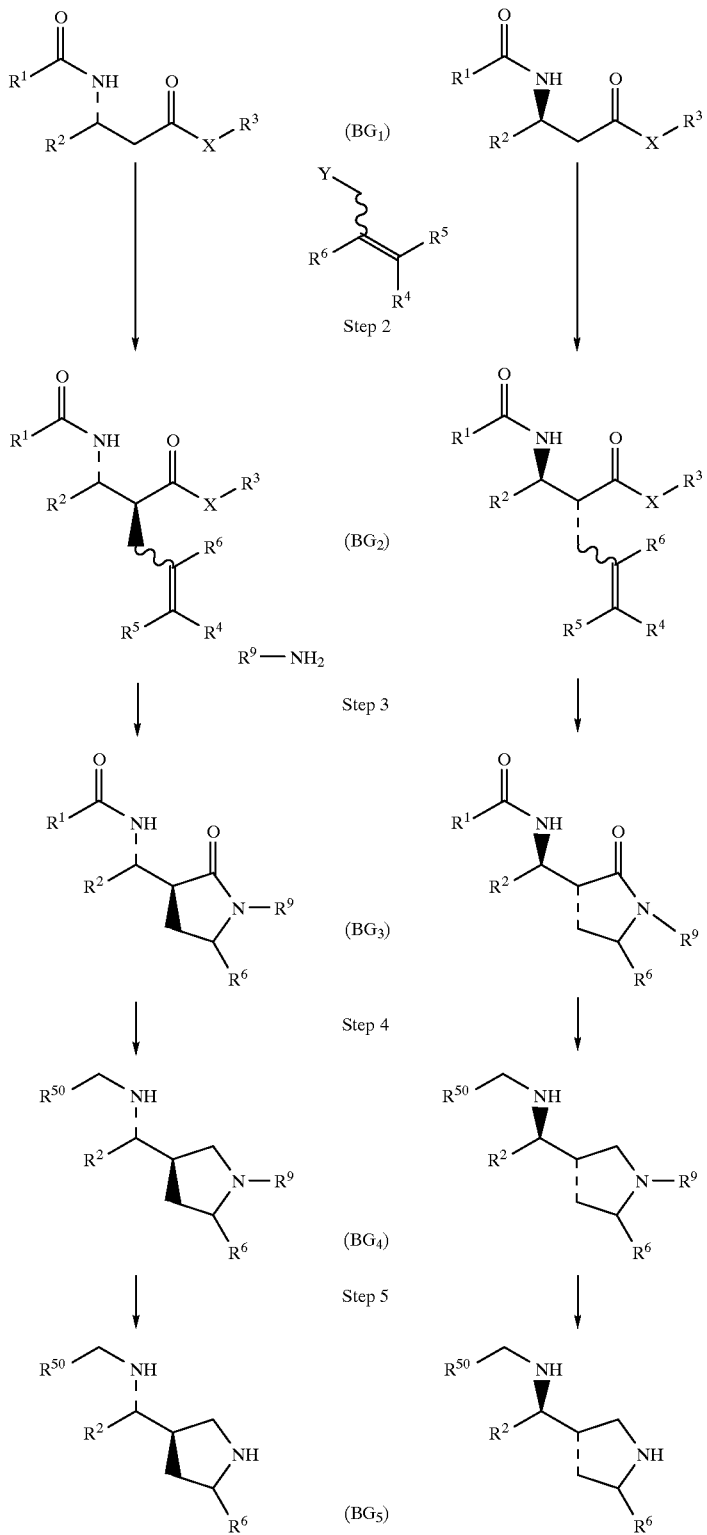

CHART BX1
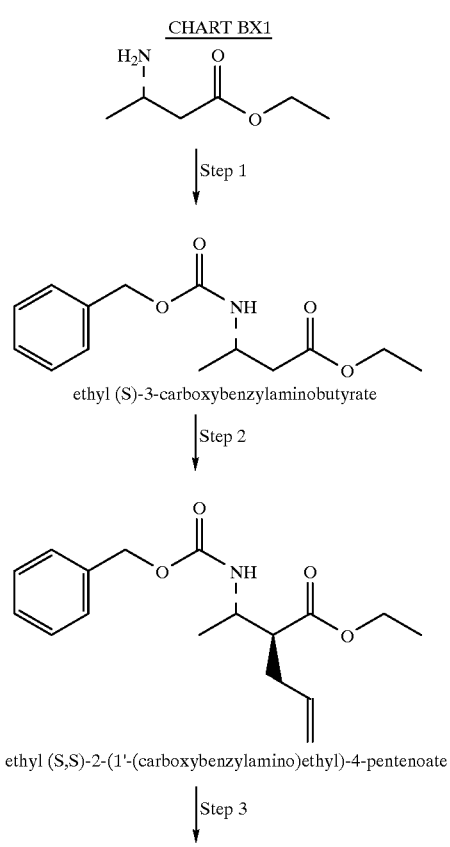
ethyl (S)-3-carboxybenzylaminobutyrate
ethyl (S,S)-2-(1'-(carboxybenzylamino)ethyl)-4-pentenoate
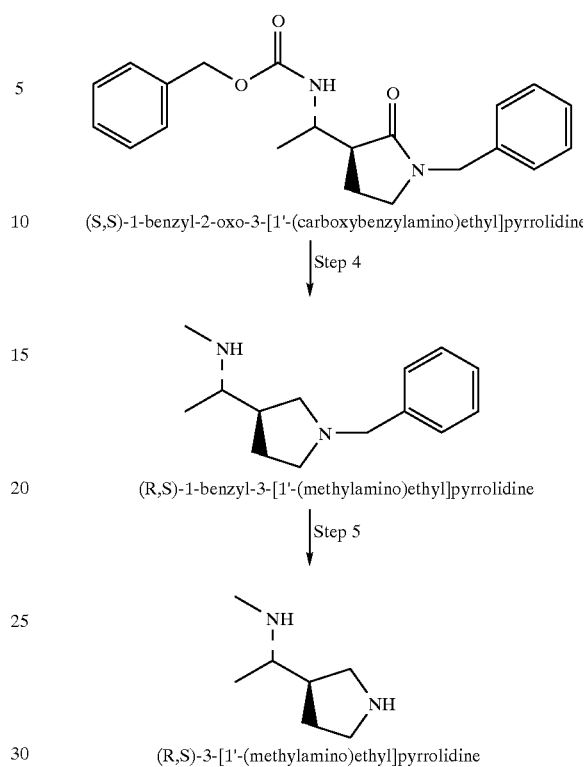
(S,S)-1-benzyl-2-oxo-3-[1'-(carboxybenzylamino)ethyl]pyrrolidine
(R,S)-1-benzyl-3-[1'-(methylamino)ethyl]pyrrolidine
(R,S)-3-[1'-(methylamino)ethyl]pyrrolidine
CHART CG
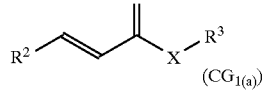
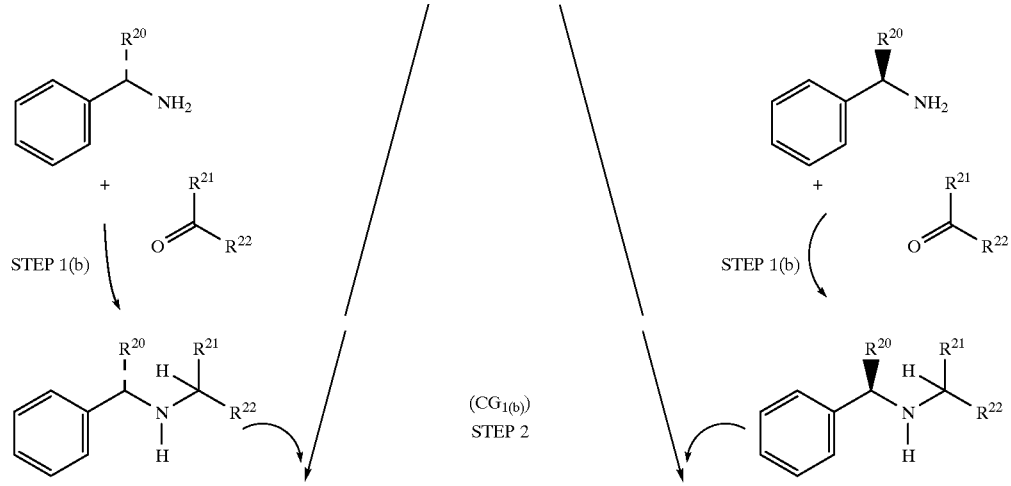

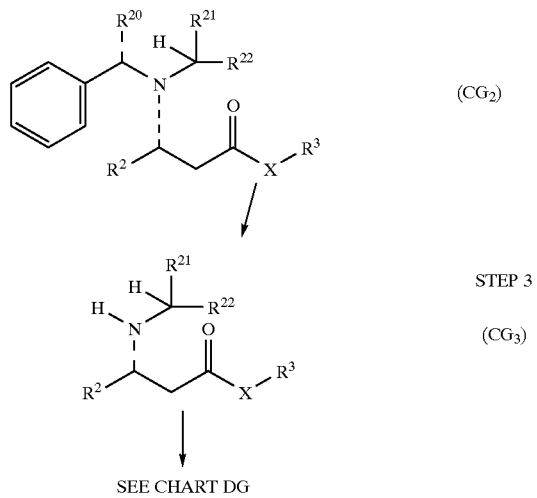
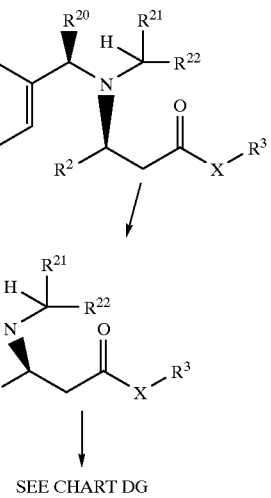
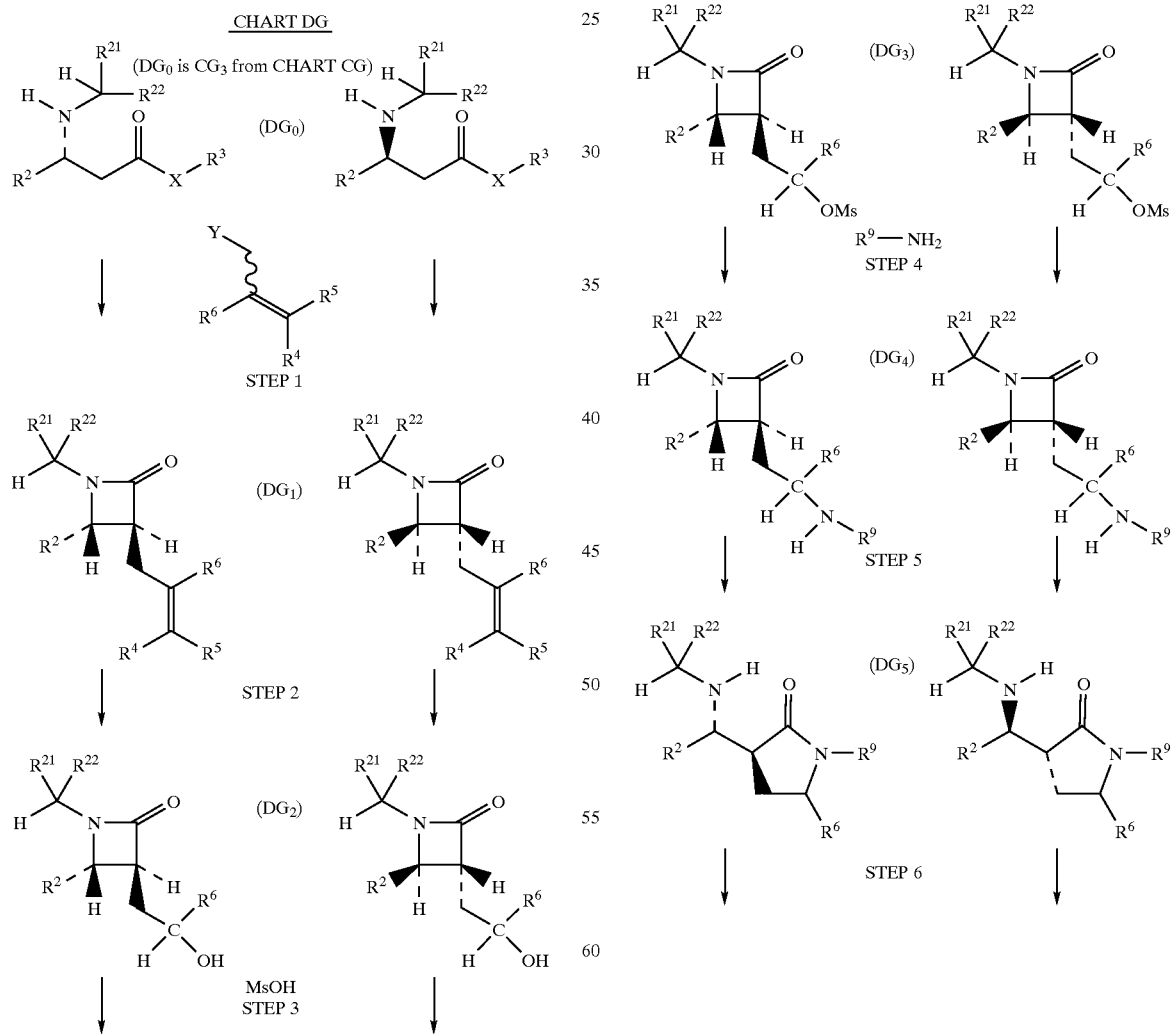

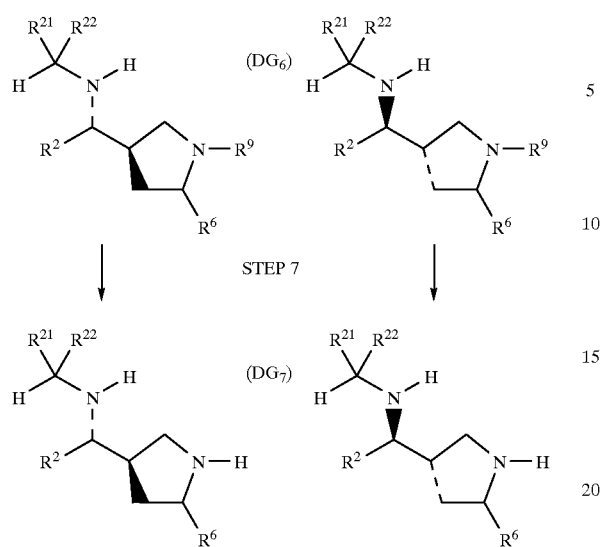
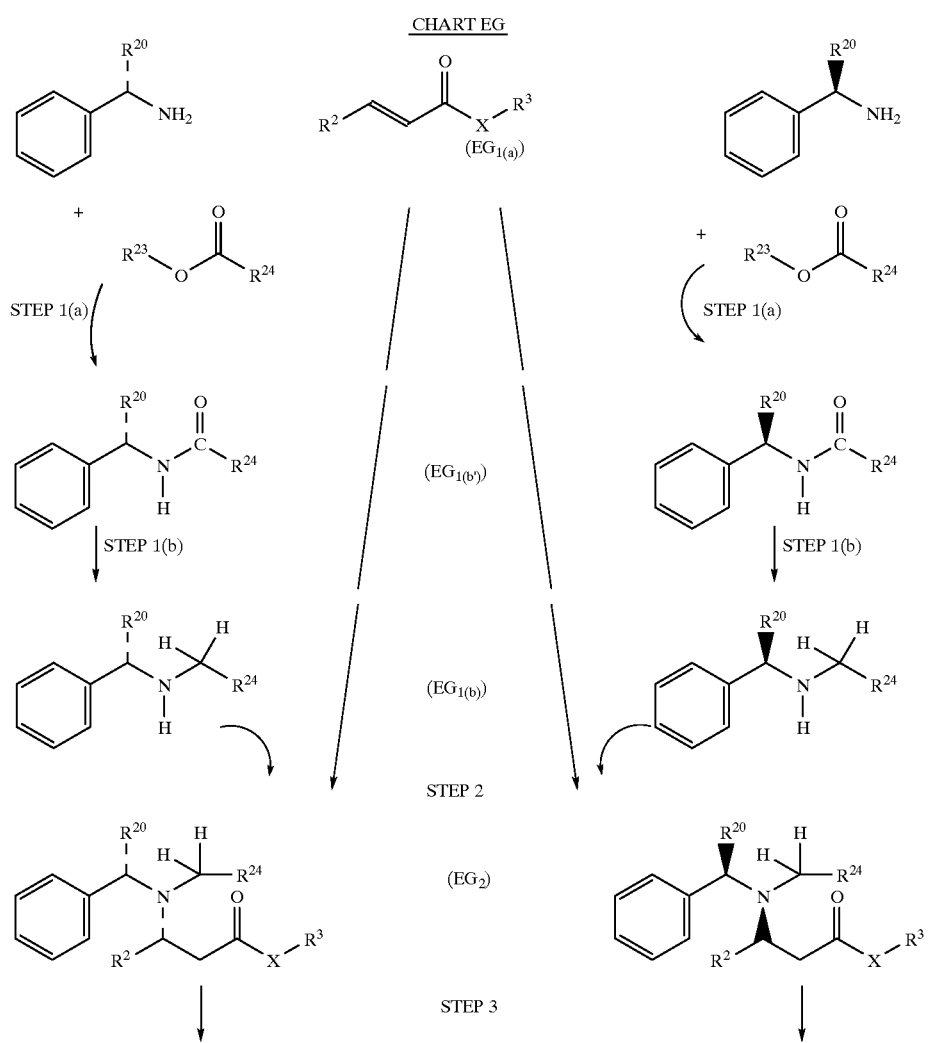
CHART EG

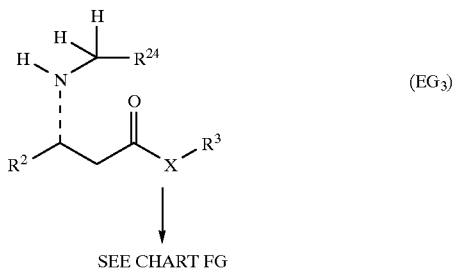
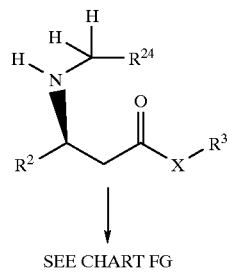
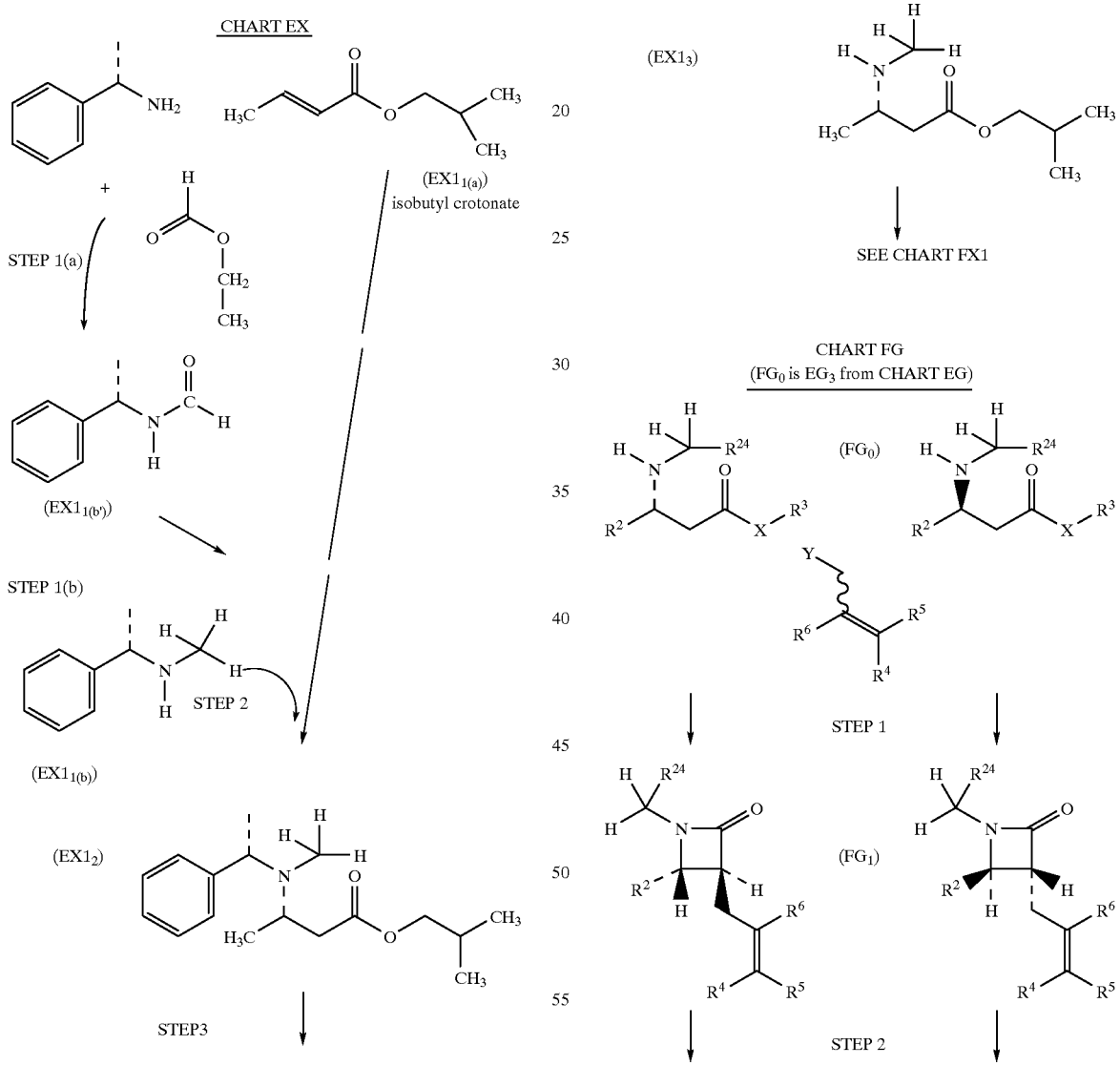

59
-continued
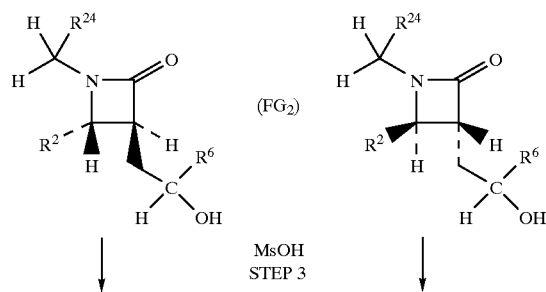
MsOH
STEP 3
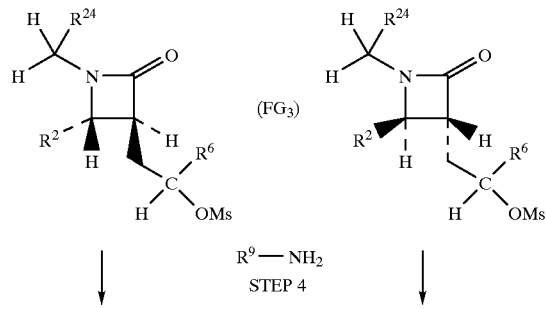
$R^9$—$NH_2$
STEP 4
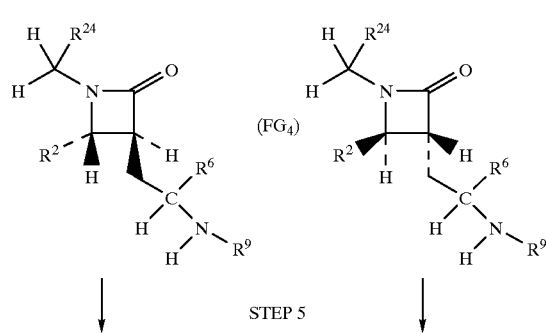
STEP 5
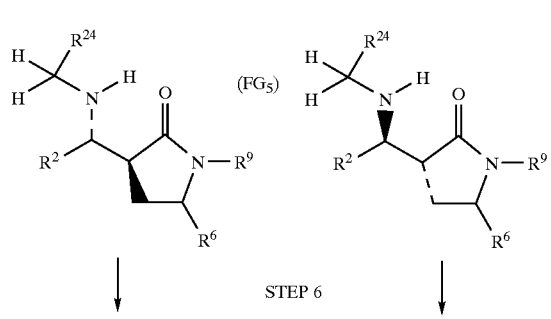
STEP 6
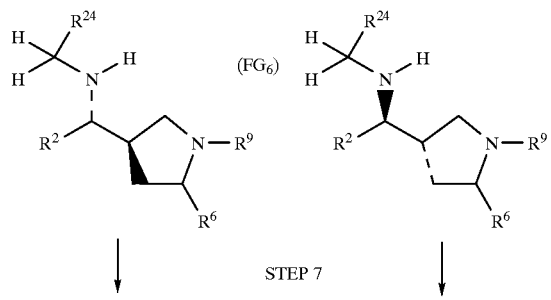
STEP 7
60
-continued
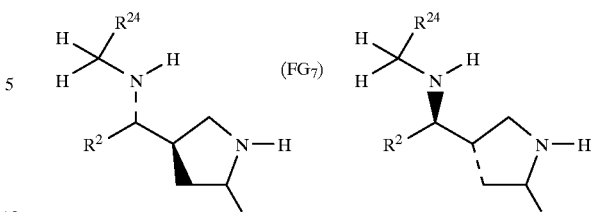
CHART FX
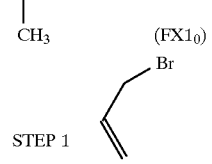
(FX1₀)
STEP 1
(FX1₁)
STEP 2
(FX1₂)
MsOH
STEP 3
(FX1₃)
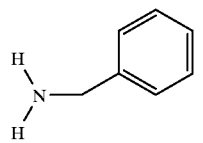
STEP 4

-continued

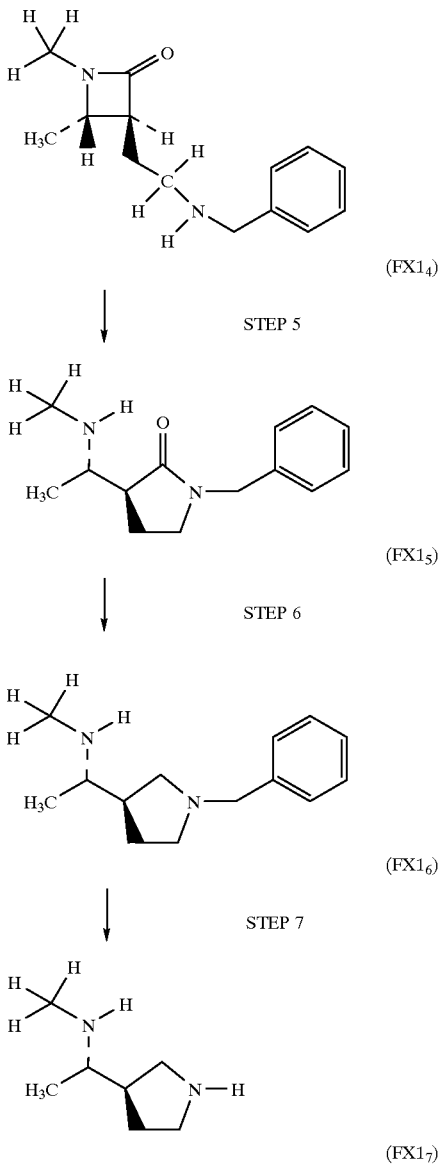

We claim:
1. A compound represented by the formulas shown in formula BG$_{4-1}$, shown below,

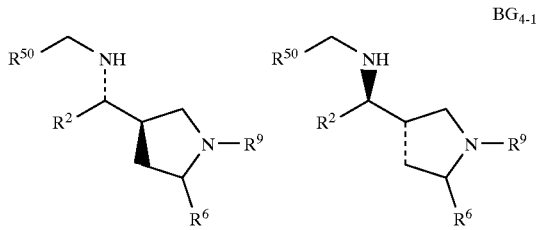

BG$_{4-1}$ where R$^{50}$ is H, —(C$_1$–C$_8$)alkyl, —(C$_3$–C$_8$)cycloalkyl, —(C$_1$–C$_8$)alkyl-(C$_3$–C$_8$)cycloalkyl, —(C$_6$–C$_{12}$ aryl), or —(C$_1$–C$_8$)alkyl-(C$_6$–C$_{12}$ aryl), wherein said aryl or alkyl may be substituted with one to three of the following groups, (C$_6$–C$_{12}$ aryl), (C$_1$–C$_3$)alkyl, (C$_1$–C$_3$) alkoxy, halogen, or trifluoromethyl, where R$^2$ is —(C$_1$–C$_8$)alkyl, —(C$_3$–C$_8$)cycloalkyl, —(C$_1$–C$_8$)alkyl-(C$_3$–C$_8$)cycloalkyl, —(C$_6$–C$_{12}$ aryl), or —(C$_1$–C$_8$)alkyl-(C$_6$–C$_{12}$ aryl), wherein said aryl or alkyl is substituted with one to three of the following groups, —(C$_6$–C$_{12}$ aryl), —(C$_1$–C$_3$)alkyl, —(C$_1$–C$_3$) alkoxy, halogen, or trifluoromethyl;

where R$^6$ is H, —(C$_1$–C$_8$)alkyl, —(C$_3$–C$_8$)cycloalkyl, —(C$_1$–C$_8$)alkyl-(C$_3$–C$_8$)cycloalkyl, —(C$_6$–C$_{12}$ aryl), —(C$_1$–C$_8$)alkyl-(C$_6$–C$_{12}$ aryl), wherein said aryl or alkyl is substituted with one to three of the following groups, —(C$_6$–C$_{12}$ aryl), —(C$_1$–C$_3$)alkyl, —(C$_1$–C$_3$) alkoxy, halogen, or trifluoromethyl;

where R$^9$ is —CH$_2$—(C$_6$)aryl, wherein said aryl may be substituted with one to three of the following groups, —(C$_6$ aryl), —(C$_1$–C$_3$)alkyl, —(C$_1$–C$_3$) alkoxy, halogen, or trifluoromethyl.

2. The compound of claim 1 comprising (R,S)-1-benzyl-3-(1'-(methylamino)ethyl)pyrrolidine, shown below,

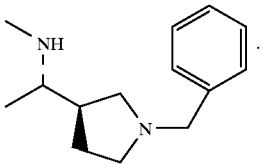

3. The compound comprising (R,S)-1-benzyl-3-(1'-(methylamino)ethyl)pyrrolidine, shown below,

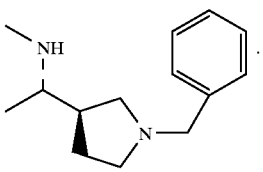

4. The process for the preparation of a compound represented by the formula on the left side, or the right side of formula BG$_{4-1}$, below, or, if starting materials in formula BG$_{3-1}$, below, are a racemic mixture, the reaction may produce a mixed ratio of compounds represented on both sides of the formula BG$_{4-1}$, below,

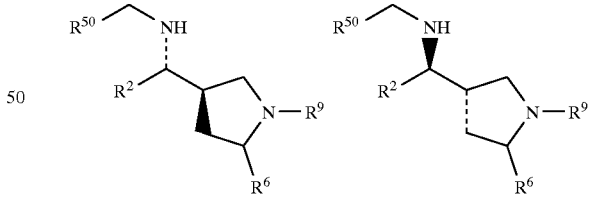

BG$_{4-1}$ where R$^{50}$ is H, —(C$_1$–C$_8$)alkyl, —(C$_3$–C$_8$)cycloalkyl, —(C$_1$–C$_8$)alkyl-(C$_3$–C$_8$)cycloalkyl, —(C$_6$–C$_{12}$ aryl), or —(C$_1$–C$_8$)alkyl-(C$_6$–C$_{12}$ aryl), wherein said aryl or alkyl may be substituted with one to three of the following groups, (C$_6$–C$_{12}$ aryl), (C$_1$–C$_3$)alkyl, (C$_1$–C$_3$) alkoxy, halogen or trifluoromethyl;

where R$^2$ is —(C$_1$–C$_8$)alkyl, —(C$_3$–C$_8$)cycloalkyl, —(C$_1$–C$_8$)alkyl-(C$_3$–C$_8$)cycloalkyl, —(C$_6$–C$_{12}$ aryl), or —(C$_1$–C$_8$)alkyl (C$_6$–C$_{12}$ aryl), wherein said aryl or alkyl may be substituted with one to three of the following groups, (C$_6$–C$_{12}$ aryl), (C$_1$–C$_3$)alkyl, (C$_1$–C$_3$) alkoxy, halogen or trifluoromethyl;

where $R^6$ is H, —($C_1$–$C_8$)alkyl, —($C_3$–$C_8$)cycloalkyl, —($C_1$–$C_8$)alkyl-($C_3$–$C_8$)cycloalkyl, —($C_6$–$C_{12}$ aryl), or —($C_1$–$C_8$)alkyl-($C_6$–$C_{12}$ aryl), wherein said aryl or alkyl may be substituted with one to three of the following groups, —($C_6$–$C_{12}$ aryl), —($C_1$–$C_3$)alkyl, —($C_1$–$C_3$) alkoxy, halogen or trifluoromethyl;

where $R^9$ is —$CH_2$—($C_6$)aryl, wherein said aryl may be substituted with one to three of the following groups, —($C_6$ aryl), —($C_1$–$C_3$)alkyl, —($C_1$–$C_3$) alkoxy, halogen or trifluoromethyl;

which comprises treating a compound represented by formula $BG_{3\text{-}1}$

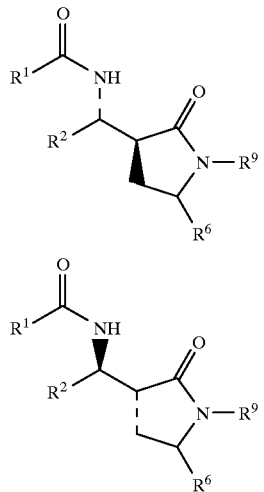

with a reducing agent, where $R^1$ is H, —($C_1$–$C_8$)alkyl, —($C_3$–$C_8$)cycloalkyl, —($C_1$–$C_8$)alkyl-($C_3$–$C_8$)cycloalkyl, —($C_6$–$C_{12}$ aryl), —($C_1$–$C_8$)alkyl-($C_6$–$C_{12}$ aryl), —O—($C_{1\text{-}8}$ alkyl), —O—($C_{3\text{-}8}$ cycloalkyl), —O—($C_{1\text{-}8}$ alkyl)($C_{3\text{-}8}$ cycloalkyl), —O—($C_{6\text{-}12}$ aryl), or —O—($C_{1\text{-}8}$ alkyl)-aryl, wherein said aryl or alkyl may be substituted with one to three of the following groups, ($C_6$–$C_{12}$ aryl), ($C_1$–$C_3$) alkyl, ($C_1$–$C_3$) alkoxy, halogen or trifluoromethyl, with the proviso that when $R^1$ is —O—($C_{1\text{-}8}$ alkyl), —O—($C_{3\text{-}8}$ cycloalkyl), —O—($C_{1\text{-}8}$ alkyl)($C_{3\text{-}8}$ cycloalkyl), —O—($C_{6\text{-}12}$ aryl), —O—($C_{1\text{-}8}$ alkyl)-aryl, then reduction with LAH, DIBAL or Borane will always produce $R^{50}$ is H.

5. A process for the preparation of (R,S)-1-benzyl-3-(1'-(methylamino)ethyl)pyrrolidine, shown below,

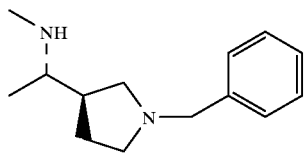

which comprises treating (S,S)-1-benzyl-2-oxo-3-(1'-(carboxybenzylamino)ethyl)pyrrolidine, shown below,

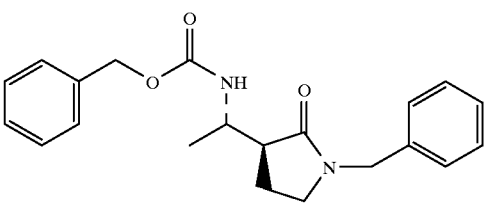

with a reducing agent, at about 0°–50° C., to produce (R,S)-1-benzyl-3-(1'-(methylamino)ethyl)pyrrolidine.

6. The process for the preparation of a compound represented by the formulas on the left side, or the right side of formula $BG_{4\text{-}1}$, below, or, if starting materials are a racemic mixture, the reaction may produce a mixed ratio of compounds represented on both sides of the formula $BG_{4\text{-}1}$, below,

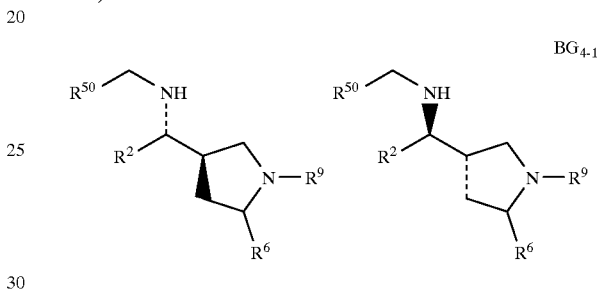

where $R^{50}$ is H, —($C_1$–$C_8$)alkyl, —($C_3$–$C_8$)cycloalkyl, —($C_1$–$C_8$)alkyl-($C_3$–$C_8$)cycloalkyl, —($C_6$–$C_{12}$ aryl), or ($C_1$–$C_8$)alkyl-($C_6$–$C_{12}$ aryl), wherein said aryl or alkyl may be substituted with one to three of the following groups, ($C_6$–$C_{12}$ aryl), ($C_1$–$C_3$)alkyl, ($C_1$–$C_3$) alkoxy, halogen or trifluoromethyl;

where $R^2$ is —($C_1$–$C_8$)alkyl, —($C_3$–$C_8$)cycloalkyl, —($C_1$–$C_8$)alkyl-($C_3$–$C_8$)cycloalkyl, —($C_6$–$C_{12}$ aryl), or —($C_1$–$C_8$)alkyl-($C_6$–$C_{12}$ aryl), wherein said aryl or alkyl may be substituted with one to three of the following groups, ($C_6$–$C_{12}$ aryl), ($C_1$–$C_3$)alkyl, ($C_1$–$C_3$) alkoxy, halogen or trifluoromethyl;

where $R^6$ is H, —($C_1$–$C_8$)alkyl, —($C_3$–$C_8$)cycloalkyl, —($C_1$–$C_8$)alkyl-($C_3$–$C_8$)cycloalkyl, —($C_6$–$C_{12}$ aryl), or —($C_1$–$C_8$)alkyl-($C_6$–$C_{12}$ aryl), wherein said aryl or alkyl may be substituted with one to three of the following groups, —($C_6$–$C_{12}$ aryl), —($C_1$–$C_3$)alkyl, —($C_1$–$C_3$) alkoxy, halogen or trifluoromethyl;

where $R^9$ is —$CH_2$—($C_6$)aryl, wherein said aryl may be substituted with one to three of the following groups, —($C_6$ aryl), —($C_1$–$C_3$)alkyl, —($C_1$–$C_3$) alkoxy, halogen or trifluoromethyl;

comprising a process for preparing a compound represented by formula $BG_{3\text{-}1}$

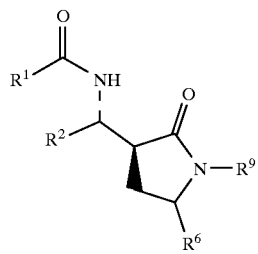

BG₃₋₁

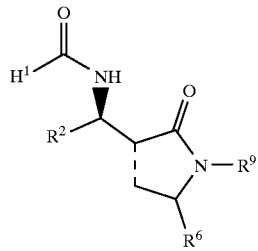

where R¹ is H, —(C₁–C₈)alkyl, —(C₃–C₈)cycloalkyl, —(C₁–C₈)alkyl-(C₃–C₈)cycloalkyl, —(C₆–C₁₂ aryl), —(C₁–C₈)alkyl-(C₆–C₁₂ aryl), —O—(C₁₋₈ alkyl), —O—(C₃₋₈ cycloalkyl), —O—(C₁₋₈ alkyl)(C₃₋₈ cycloalkyl), —O—(C₆₋₁₂ aryl), —O—(C₁₋₈ alkyl)-aryl, wherein said aryl or alkyl may be substituted with one to three of the following groups, (C₆–C₁₂ aryl), (C₁–C₃)alkyl, (C₁–C₃) alkoxy, halogen or trifluoromethyl, with the proviso that when R¹ is —O—(C₁₋₈ alkyl), —O—(C₃₋₈ cycloalkyl), —O—(C₁₋₈ alkyl)(C₃₋₈ cycloalkyl), —O— (C₆₋₁₂ aryl), or —O—(C₁₋₈ alkyl)-aryl, then reduction with LAH, DIBAL or Borane will always produce R⁵⁰ is H;

where R², R⁶ and R⁹ are defined above;

which comprises subjecting to ozonolysis a compound represented by formula

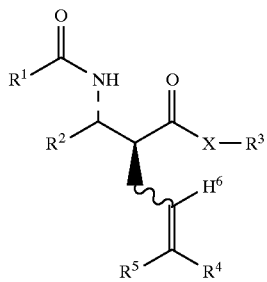

BG₂

-continued

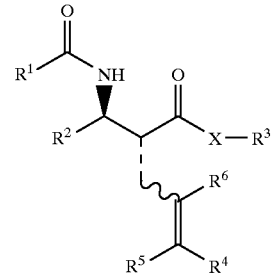

where R³ is —(C₁–C₈)alkyl, —(C₃–C₈)cycloalkyl, —(C₁–C₈)alkyl-(C₃–C₈)cycloalkyl, —(C₆–C₁₂ aryl), or —(C₁–C₈)alkyl-(C₆–C₁₂ aryl), wherein said aryl or alkyl may be substituted with one to three of the following groups, —(C₆–C₁₂ aryl), —(C₁–C₃)alkyl, —(C₁–C₈) alkoxy, halogen, or trifluoromethyl;

where, R⁴, R⁵ and R⁶ independently are H, (C₁–C₈)alkyl, or (C₁–C₈)alkyl (C₆–C₁₂)aryl, wherein said aryl may be substituted with one to three of any of the following groups: (C₆–C₁₂) aryl, C₁–C₃ alkoxy, C₁–C₃ alkyl, trifluoromethyl, fluoro, chloro, or bromo;

X is O, NH, or S, followed by reaction with R⁹—NH₂, under reducing conditions, such as with sodium cyano borohydride, sodium triacetoxy borohydride or sodium borohydride, (in order of preference) at about 0° to 50° C., to produce a compound represented by formula BG₃₋₁

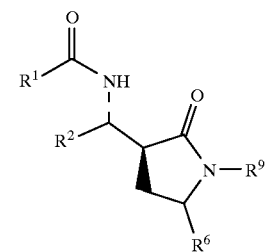

BG₃₋₁

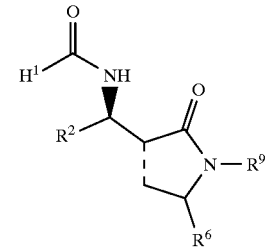

and then treating the compounds of BG₃₋₁ with a reducing agent to produce the desired compounds, where R¹ is as defined above; to produce the compounds of BG₄₋ₗ.

* * * * *